United States Patent
Hayashi et al.

[11] 4,140,712
[45] Feb. 20, 1979

[54] 20-HYDROXY-PROSTAGLANDINS

[75] Inventors: Masaki Hayashi; Seiji Kori, both of Takatsuki; Hajimu Miyake, Suita, all of Japan

[73] Assignee: Ono Pharmaceutical Company, Osaka, Japan

[21] Appl. No.: 547,293

[22] Filed: Feb. 5, 1975

[30] Foreign Application Priority Data

Feb. 13, 1974 [GB] United Kingdom ............... 6610/74

[51] Int. Cl.$^2$ ........................... C07C 177/00
[52] U.S. Cl. .................... 562/503; 260/345.7 P; 260/347.3; 424/305; 424/317; 542/426; 560/121
[58] Field of Search .................. 260/514 D, 468 D; 560/121

[56] References Cited

U.S. PATENT DOCUMENTS

| | | | |
|---|---|---|---|
| 3,843,713 | 10/1974 | Finch et al. | 260/468 |
| 3,878,239 | 4/1975 | Hayashi et al. | 260/514 |

FOREIGN PATENT DOCUMENTS 826090  6/1975  Belgium ................... 260/514

*Primary Examiner*—Robert Gerstl
*Attorney, Agent, or Firm*—Albert H. Graddis; Frank S. Chow

[57] ABSTRACT

The present invention relates to 20-hydroxy prostaglandins of the formula:

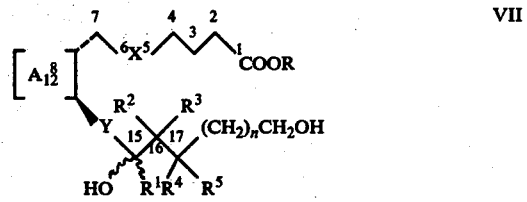

wherein A represents a grouping of the formula:

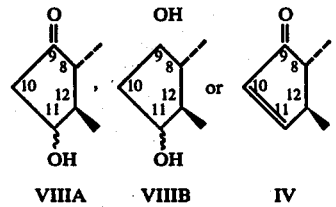

and X represents ethylene or cis-vinylene and Y represents trans-vinylene, or X and Y each represent ethylene, R represents a hydrogen atom or a straight- or branched-chain alkyl group containing from 1 to 12 carbon atoms, $R^1$, $R^2$, $R^3$, $R^4$ and $R^5$, which may be the same or different, each represent a hydrogen atom or a methyl or ethyl group, and n represents zero or an integer from 1 to 3 inclusive, and cyclodextrin clathrates of such acids and esters and, when R represents a hydrogen atom, the non-toxic salts thereof.

These compounds exhibit characteristic prostaglandin activity.

11 Claims, No Drawings

20-HYDROXY-PROSTAGLANDINS

This invention is concerned with new prostaglandin analogues.

Prostaglandins are derivatives of prostanoic acid which has the following formula:

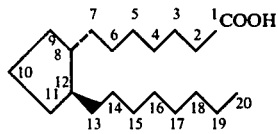

Various types of prostaglandins are known, the types depending inter alia on the structure and substituents on the alicyclic ring. For example, the alicyclic rings of prostaglandins E(PGE), F(PGF) and A(PGA) have the structures:

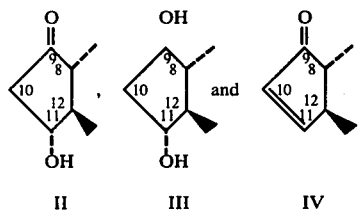

respectively. The dotted lines in the foregoing formulae and in other formulae throughout this specification denote, in accordance with generally accepted rules of nomenclature, that the attached grouping lies behind the general plane of the ring system, i.e. that the grouping is in α-configuration, that the thickened lines denote that the grouping lies in front of the general plane of the system, i.e. that the grouping is in β-configuration, and that the wavy line indicates that the grouping is in α- or β-configuration.

Such compounds are sub-classified according to the position of double bond(s) in the side chain(s) attached to the 8- and 12-positions of the alicyclic ring. Thus $PG_1$ compounds have a trans-double bond between $C_{13}-C_{14}$ (trans-$\Delta^{13}$) and $PG_2$ compounds have a cis-double bond between $C_5-C_6$ and a trans-double bond between $C_{13}-C_{14}$ (cis-$\Delta^5$, trans-$\Delta^{13}$). For example, prostaglandin $F_{1\alpha}$ ($PGF_{1\alpha}$) and prostaglandin $E_1$ ($PGE_1$) are characterized by the following structures V and VI.

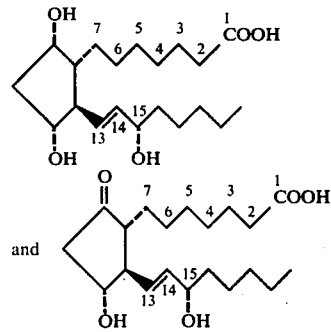

respectively. The structures of $PGF_{2\alpha}$ and $PGE_2$, as members of the $PG_2$ group, correspond to those of formulae V and VI respectively with a cis-double bond between the carbon atoms in positions 5 and 6. Compounds in which the double bond between the carbon atoms in positions 13 and 14 of members of the $PG_1$ group is replaced by ethylene are known as dihydro-prostaglandins, e.g. dihydro-prostaglandin-$F_{1\alpha}$ (dihydro-$PGF_{1\alpha}$) and dihydro-prostaglandin-$E_1$ (dihydro-$PGE_1$).

Moreover, when one or more methylene groups are added to, or eliminated from, the aliphatic group attached to the 12-position of the alicyclic ring of the prostaglandins the compounds are known, in accordance with the usual rules of organic nomenclature, as ω-homoprostaglandins (methylene group added) or ω-norprostaglandins (methylene group eliminated), and, when more than one methylene group is added or eliminated, the number is indicated by di-, tri- etc. before the prefix "homo" or "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGE's and PGA's have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia.

$PGE_1$ inhibits blood platelet aggregation and also removes the thrombus and prevents thrombosis. PGE's and PGF's have a stimulating effect on smooth muscle and increase the intestinal peristalsis; these actions indicate therapeutic utility on post-operative ileus and as purgatives. Furthermore, PGE's and PGF's may be used as oxytocics, as abortifacients in the first and second trimesters; in the post-labour abortion of the placenta, and as oral contraceptives because they regulate the sexual cycle of female mammals. PGE's and PGA's have vasodilator and diuretic activities. PGE's are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such properties to an enhanced degree, or hitherto unknown pharmacological properties. It has now been found after research and experimentation that by introducing a hydroxy group in the 20-position of prostaglandins E, F and A and certain analogues thereof, the pharmacological properties of the 'natural' prostaglandins may, in some aspects of their activities, be improved or modified.

The present invention accordingly provides the new prostaglandin analogues of the general formula:

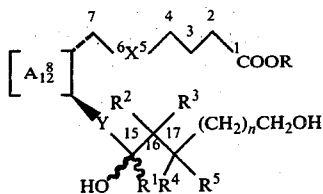

VII

[wherein A represents a grouping of formula IV as indicated above or a grouping of the formula:

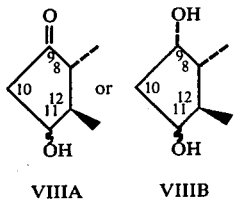

VIIIA   VIIIB

X represents ethylene (i.e. —CH$_2$CH$_2$—) of cis-vinylene (i.e. —CH=CH—) and Y represents trans-vinylene or X and Y each represent ethylene, R represents a hydrogen atom or a straight- or branched-chain alkyl group containing from 1 to 12 carbon atoms (preferably methyl), R$^1$, R$^2$, R$^3$, R$^4$ and R$^5$, which may be the same or different, each represent a hydrogen atom or a methyl or ethyl group, and n represents zero or an integer from 1 to 3 inclusive] and cyclodextrin clathrates of such acids and esters and, when R represents a hydrogen atom, non-toxic (e.g. sodium) salts thereof. Preferably the hydroxy group attached to the C-15 carbon atom of formula VII is in α-configuration, and the hydroxy groups attached to the 11-positions of the cyclopentane rings of formulae VIIIA and VIIIB are also in the α-configuration.

The present invention is concerned with all compounds of general formula VII in the 'natural' form or its enantiomeric form, or mixtures thereof, more particularly the racemic form consisting of equimolecular mixtures of natural and its enantiomeric form.

As will be apparent to those skilled in the art, the compounds depicted in general formula VII have at least three centres of chirality, these three centres of chirality being at the alicyclic ring carbon atoms of group A identified as 8 and 12 and at the C-15 carbon atom which has attached to it a hydroxy group. Still further centres of chirality occur when the alicyclic group A carries a hydroxy group on the carbon atom in position 11 (i.e. when the ring is that of formula VIIIA) or hydroxy groups in positions 9 and 11 (i.e. when the ring is that of formula VIIIB) and further centres of chirality occur at positions 16 and 17 when at least one of the symbols R$^2$, R$^3$, R$^4$ and R$^5$ represents a methyl or ethyl group. The presence of chirality leads, as is well known, to the existence of isomerism. However, the compounds of general formula VII all have such a configuration that the side-chains attached to the ring carbon atoms in the positions identified as 8 and 12 are trans with respect to each other. Accordingly, all isomers of general formula VII, and mixtures thereof, which have those side-chains attached to the ring carbon atoms in positions 8 and 12 in the trans-configuration and have a hydroxy group as depicted in the 15-position are to be considered within the scope of general formula VII.

According to a feature of the present invention, the prostaglandin analogues of general formula VII wherein A represents a grouping of formula VIIIA or VIIIB, R represents a hydrogen atom and the other symbols are as hereinbefore defined, are obtained by the process which comprises the hydrolysis to hydroxy groups of the groups —OR$^6$ of a cyclopentane derivative of the general formula:

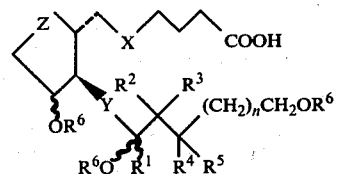

IX wherein X, Y, R$^1$, R$^2$, R$^3$, R$^4$, R$^5$ and n are as hereinbefore defined, Z represents

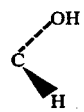

or C=O, and R$^6$ represents a 2-tetrahydrofuranyl group, a 1-ethoxyethyl group or, preferably, a 2-tetrahydropyranyl group unsubstituted or substituted by at least one alkyl group. The —OR$^6$ groups of the compounds of formula IX may be converted to hydroxy groups by mild hydrolysis with an aqueous solution of an organic acid, e.g. acetic acid, or with a dilute inorganic acid, e.g. hydrochloric acid, for example by treatment of the compounds of formula IX at a temperature ranging from ambient to 60° C. (preferably at a temperature below 45° C.) with an aqueous solution of an organic acid, e.g. acetic acid, or with a dilute inorganic acid, e.g. hydrochloric acid, in the presence of an organic solvent miscible with water, for example a lower alkanol or tetrahydrofuran.

The cyclopentane derivatives of general formula IX employed as starting materials in the aforesaid process are new compounds and as such constitute a feature of the present invention.

According to a further feature of the present invention, the prostaglandin analogues of general formula VII wherein A represents a grouping of formula IV, R represents a hydrogen atom and the other symbols are as hereinbefore defined, are prepared by the process which comprises converting by methods known per se the alicyclic ring A of a compound of formula VII, wherein A represents a grouping of formula VIIIA, R represents a hydrogen atom and the other symbols are as hereinbefore defined, into an alicyclic ring A of formula IV, for example by subjecting the compound of formula VII wherein A represents a grouping of formula VIIIA, R represents a hydrogen atom and the other symbols are as hereinbefore defined, to dehydration using an aqueous solution of an organic or inorganic acid having a higher concentration than that employed for hydrolysis of compounds of general formula IX, e.g. 1N hydrochloric acid, if desired in the presence of cupric chloride, or acetic acid, and heating at a temperature of 30°-60° C.

According to another feature of the present invention, the cyclopentane derivatives of formula IX, wherein Z represents C=O and the other symbols are as hereinbefore defined, are prepared from compounds of formula IX wherein Z represents

The processes hereinbefore described for the preparation of prostaglandin analogues of general formula VII, wherein R represents a hydrogen atom and the other symbols are as hereinbefore defined, may thus be represented by the series of reactions depicted schematically below in Scheme A.

SCHEME A

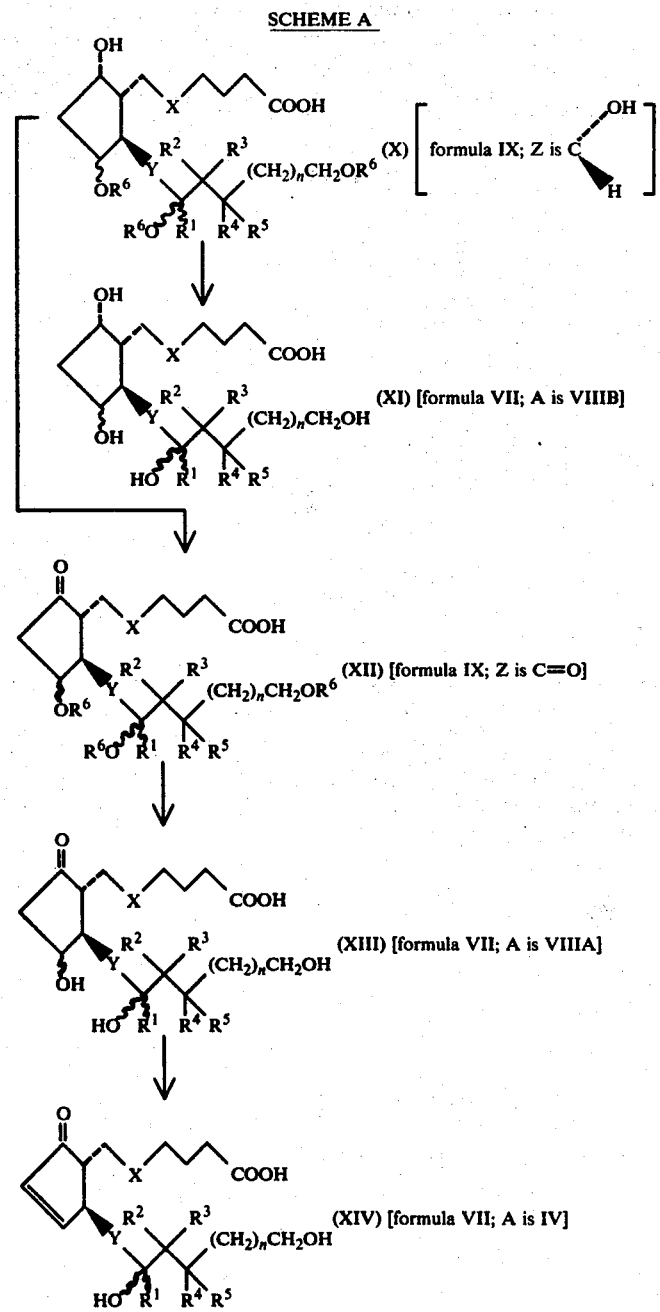

and the other symbols are as hereinbefore defined by methods known per se for the conversion of a hydroxy group in the 9-position of a prostaglandin compound to an oxo group, for example by means of a chromic acid solution (e.g. obtained from chromium trioxide, manganese sulphate, sulphuric acid and water) or Jones' reagent.

wherein the various symbols are as hereinbefore defined.

Compounds of general formula X wherein X represents cis-vinylene may, if desired, be converted into corresponding compounds of general formula X wherein X represents ethylene and Y represents trans-vinylene or ethylene by reduction, and also compounds of general formula X wherein X represents cis-vinylene and Y represents trans-vinylene may be converted into corresponding compounds of general formula X wherein X and Y both represent ethylene by reduction. Suitably, the reductions may be effected by catalytic hydrogenation in the presence of a hydrogenation catalyst and in the presence of an inert organic solvent, for example a lower alkanol, e.g. methanol or ethanol, at laboratory temperature at normal or elevated pressure, e.g. at a hydrogen pressure from atmospheric to 15 kilogrammes per square centimeter. When it is desired to reduce only the cis-vinylene group X and leave unaffected a trans-vinylene group Y, the hydrogenation catalyst may be, for example, palladium on charcoal or palladium black, the hydrogenation being monitored to avoid any reduction of the trans-vinylene group Y. When it is desired to reduce the cis-vinylene group X and simultaneously Y in general formula X represents ethylene, an alternative hydrogenation catalyst is platinum dioxide. When it is desired to reduce X as cis-vinylene and Y as trans-vinylene to obtain compounds of general formula X wherein X and Y both represent ethylene, platinum oxide as catalyst is satisfactory for this purpose, and the hydrogenation is carried out until two times the molar quantity of hydrogen has been consumed.

Compounds of general formula X, i.e. the compounds of general formula IX wherein Z is

and the other symbols are as hereinbefore defined, may be prepared by the hydrolysis under alkaline conditions of a compound of the general formula:

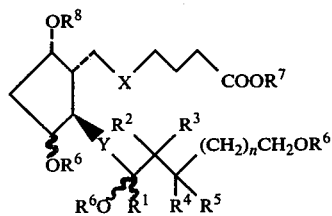 XV wherein X, Y, $R^1$, $R^2$, $R^3$, $R^4$, $R^5$, $R^6$ and n are as hereinbefore defined, $R^7$ represents a lower alkyl group, preferably containing from 1 to 4 carbon atoms, and $R^8$ represents an alkylcarbonyl group wherein the alkyl moiety preferably contains from 1 to 4 carbon atoms, for example an acetyl group. The hydrolysis under alkaline conditions may be effected, for example, with an aqueous solution of an alkali metal, e.g. sodium or potassium, hydroxide or carbonate in the presence of an organic solvent miscible with water, e.g. a lower alkanol or tetrahydrofuran.

Compounds of general formula XV wherein Y represents trans-vinylene and the various other symbols are as hereinbefore defined may be prepared by the reaction of a compound of the general formula:

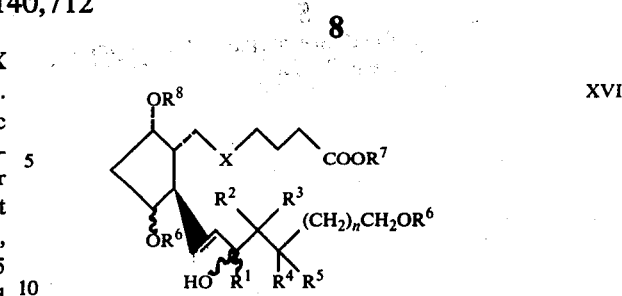 XVI (wherein the various symbols are as hereinbefore defined) with a dihydropyran, dihydrofuran or ethyl vinyl ether in an inert organic solvent, e.g. methylene chloride, in the presence of a condensing agent, e.g. p-toluenesulphonic acid.

Compounds of general formula XV wherein X and Y each represent ethylene and the various other symbols are as hereinbefore defined may be prepared by the reduction of a compound of general formula XVI (wherein the various symbols are as hereinbefore defined) to give a compound of the general formula:

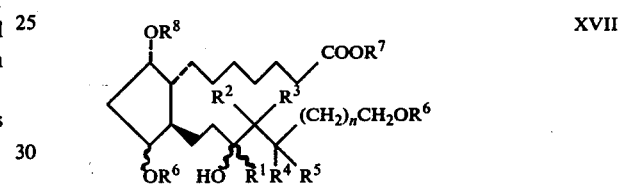 XVII (wherein the various symbols are as hereinbefore defined), which may then be reacted with a dihydropyran, dihydrofuran or ethyl vinyl ether in an inert organic solvent, e.g. methylene chloride, in the presence of a condensing agent, e.g. p-toluenesulphonic acid, to give a compound of general formula XV wherein each of X and Y represents ethylene, and the other symbols are as hereinbefore defined.

Suitably the reduction of compounds of general formula XVI may be effected by hydrogenation in the presence of a hydrogenation catalyst, for example palladium on charcoal, palladium black or platinum dioxide, in the presence of an inert organic solvent, for example a lower alkanol, e.g. methanol or ethanol, at laboratory temperature at normal or elevated pressure, e.g. at a hydrogen pressure from atmospheric to 15 kilogrammes per square centimeter.

Compounds of general formula XVI wherein $R^1$ represents a hydrogen atom and the various other symbols are as hereinbefore defined may be prepared by the reduction of a compound of the general formula:

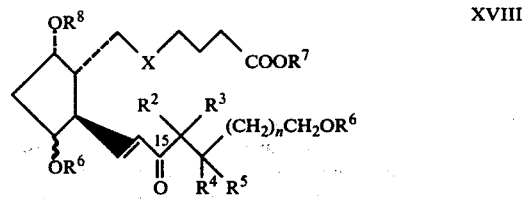 XVIII wherein the various symbols are as hereinbefore defined, to convert the carbonyl group in the 15-position to hydroxymethylene i.e.

Reduction is suitable effected with excess sodium borohydride in a lower alkanol, e.g. methanol, at a low temperature, preferably at −30° C. to −60° C., or with zinc borohydride in a suitable inert organic solvent, e.g. dimethoxyethane, at a temperature of −10° C. to 10° C. The product of general formula XVI wherein $R^1$ represents a hydrogen atom thus obtained by the reduction of a compound of formula XVIII is a mixture of isomers in which the hydroxy group at position 15 is in α- or β-configuration. If desired, the isomer having the hydroxy group in α-configuration may be separated from the isomer having the hydroxy group in β-configuration by column chromatography of the mixture on silica gel. The separated isomers may be utilised in the procedures hereinbefore described to give cyclopentane derivatives in which the hydroxy group in position 15 is in α- or β-configuration.

Compounds of general formula XVI wherein $R^1$ represents a methyl or ethyl group and the various other symbols are as hereinbefore defined may be prepared by reacting a compound of general formula XVIII (wherein the various symbols are as hereinbefore defined) with a Grignard reagent of the general formula:

$$R^9MgHal \qquad\qquad XIX$$

wherein $R^9$ represents a methyl or ethyl group and Hal represents a bromine or iodine atom. The reaction is preferably effected in diethyl ether at a temperature of −10° C. to 10° C.

Compounds of general formula XVIII may be prepared by the reaction of a compound of the general formula:

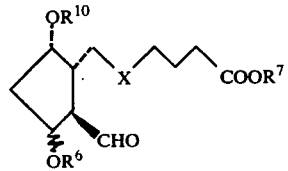

XX (wherein X, $R^6$ and $R^7$ are as hereinbefore defined, and $R^{10}$ represents a hydrogen atom or an alkylcarbonyl group containing from 1 to 4 carbon atoms, for example an acetyl group) with the sodio derivative of a dialkyl phosphonate compound of the general formula:

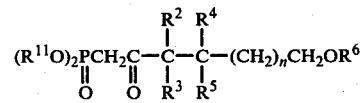

XXI wherein $R^2$, $R^3$, $R^4$, $R^5$, $R^6$ and n are as hereinbefore defined, and $R^{11}$ represents a lower alkyl group, preferably containing from 1 to 4 carbon atoms, e.g. a methyl or ethyl group. The reaction is preferably effected by suspending sodium hydride in an inert solvent, e.g. tetrahydrofuran or dimethoxyethane, and adding the dialkyl phosphonate of formula XXI. The resulting sodio derivative of the dialkyl phosphonate may be reacted with the compound of formula XX at room temperature for one to five hours to form the trans-enone compound of formula XVIII stereospecifically. Compounds thus obtained from compounds of formula XX wherein $R^{10}$ represents a hydrogen atom may then be treated with an appropriate acylating agent, for example an acid halide derived from an alkanoic acid containing from 1 to 4 carbon atoms, e.g. acetyl chloride in the presence of pyridine in methylene chloride, to give the corresponding compounds of formula XVIII wherein $R^8$ represents an alkylcarbonyl group.

The compounds of general formula XX wherein $R^{10}$ represents a hydrogen atom, $R^6$ and $R^7$ are as hereinbefore defined and the group $OR^6$ is in α-configuration (hereinafter depicted in general formula XXA), used as starting materials in the hereinbefore described procedures, may themselves be prepared from the known compounds of formula XXII below (the racemic form of the compound of formula XXII is described in J. Amer. Chem. Soc. 91, 5675 (1969) and the natural configuration compound of formula XXII is described in J. Amer. Chem. Soc. 92, 397 (1970)) by the method which may be represented by the series of reactions depicted schematically below in Scheme B:

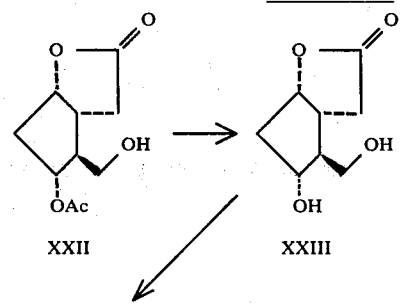

SCHEME B

SCHEME B

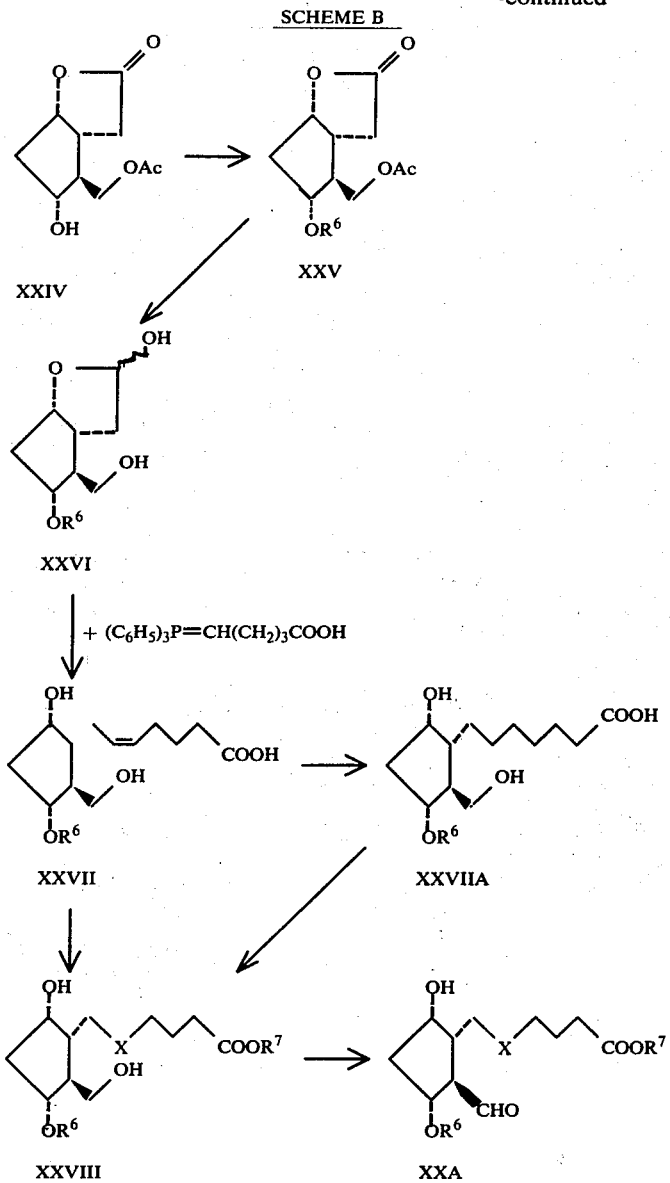

wherein $R^6$ and $R^7$ are as hereinbefore defined, and Ac represents the acetyl group, i.e. —COCH$_3$.

Compounds of formula XXIII may be prepared by hydrolysis under alkaline conditions of compounds of formula XXII. Compound of formula XXIV may be obtained by the acetylation of compounds of formula XXIII under mild conditions and may be converted into compounds of formula XXV by reaction with a dihydropyran, dihydrofuran or ethyl vinyl ether in an inert solvent, e.g. methylene chloride, in the presence of a condensing agent, e.g. p-toluenesulphonic acid. Compounds of formula XXVI may be prepared by reducing compounds of formula XXV with diisobutylaluminium hydride in toluene for about 15 minutes at −60° C. Dimsyl anion, previously prepared from sodium hydride and dimethyl sulphoxide is reacted with 4-carboxy-n-butyltriphenylphosphonium bromide to form 4-carboxy-n-butylidenetriphenylphosphorane. To that compound is added a compound of formula XXVI and the mixture in dimethyl sulphoxide is made to react for 2 hours at room temperature to yield a compound of formula XXVII.

Compounds of formula XXVII may, if desired, be reduced to give compounds of formula XXVIIA. Suitably, the reduction may be effected by hydrogenation in the presence of a hydrogenation catalyst as hereinbefore described for the reduction of compounds of formula XVI to compounds of formula XVII. Compounds of formulae XXVII or XXVIIA are then reacted with a diazoalkane in a suitable inert solvent, e.g. diethyl ether, to give compounds of formula XXVIII. Compounds of formula XXVIII may be oxidized to compounds XXA under mild and neutral conditions, e.g. with chromium trioxidepyridine complex and at a moderately low temperature. These conditions for oxidation are preferable in order to form the formyl group selectively and avoid excessive oxidation of the secondary alcohol group.

The compounds of general formula XX wherein X represents cis-vinylene, $R^{10}$ represents an alkylcarbonyl group containing from 1 to 4 carbon atoms, for example an acetyl group, $R^6$ and $R^7$ are as hereinbefore defined and the group $OR^6$ is in α-configuration (hereinafter depicted in general formula XXB), used as starting materials in the hereinbefore described procedures, may themselves be prepared by methods known per se from compounds of general formula XXVIII wherein X represents cis-vinylene by the series of reactions depicted schematically below in Scheme C:

SCHEME C

XXVIII (X = cis-vinylene)

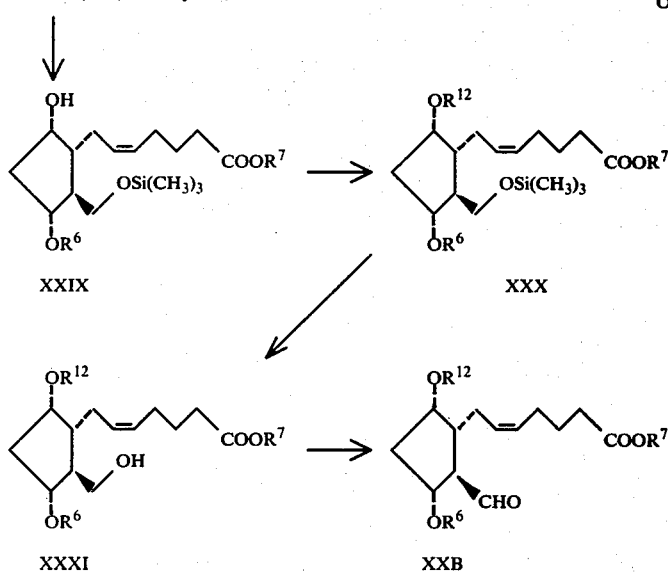

wherein $R^6$ and $R^7$ are as hereinbefore defined, and $R^{12}$ represents an alkylcarbonyl group containing from 1 to 4 carbon atoms, for example an acetyl group.

Compounds of formula XXIX may be prepared by reacting a compound of formula XXVIII with trimethylchlorosilane in an inert organic solvent, for example methylene chloride, in the presence of a base, for example pyridine or a tertiary amine, at a low temperature, e.g. at a temperature of −30° C. to 0° C. Compounds of formula XXX may be prepared by reacting a trimethylsilyl ether of formula XXIX with the appropriate acyl chloride or acid anhydride in an inert organic solvent, for example methylene chloride, in the presence of a base, for example pyridine or a tertiary amine, at a low temperature, e.g. at a temperature of 0° C. to 30° C. Compounds of formula XXXI may be prepared by treating a compound of formula XXX by methods known per se for the removal of the trimethylsilyl group, for example by treatment with an acid; it is preferable not to use a strong acid in order to avoid the risk of the removal of the group $R^6$. The compounds of formula XXXI may be oxidized to compounds of formula XXB under mild and neutral conditions, e.g. with chromium trioxide-pyridine complex or Jones' reagent and at a moderately low temperature. These conditions for oxidation are preferable in order to form the formyl group selectively and avoid excessive oxidation of the secondary alcohol group.

The compounds of general formula XX wherein X represents cis-vinylene, $R^6$, $R^7$ and $R^{10}$ are as hereinbefore defined and the group $OR^6$ is in β-configuration, which may be used as starting materials in the hereinbefore described procedures, may themselves be prepared by the series of reactions depicted in Schemes B and C but replacing the compounds of formula XXII by compounds of the formula:

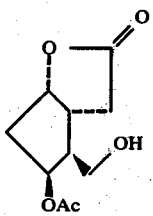

XXXII wherein Ac is as hereinbefore defined.

A method for the preparation of the bicyclo-octane starting materials of formula XXXII, wherein Ac is as hereinbefore defined, utilising known procedures may be represented by the series of reactions depicted schematically below in Scheme D (cf. E. J. Corey and Shiro Terashima, Tetrahedron Letters, No. 2, pp. 111–113, 1972):

SCHEME D

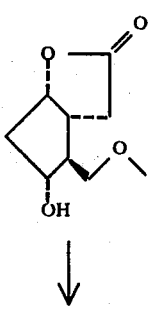

XXXIII

-continued SCHEME D

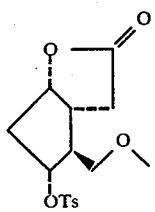

XXXIV

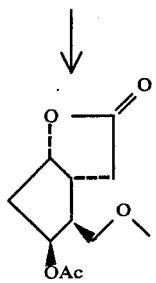

XXXV

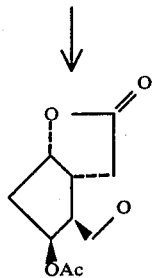

XXXVI wherein Ac is as hereinbefore defined, and Ts represents the tosyl group. The various reactions depicted above in Scheme D may be effected by methods known per se. Compounds of formula XXXV may be prepared by reacting compounds of formula XXXIV with tetraethylammonium acetate.

The compounds of general formula XXI, wherein $R^2$, $R^3$, $R^4$, $R^5$, $R^6$, $R^{11}$ and n are as hereinbefore defined, may be prepared by reacting a compound of the general formula:

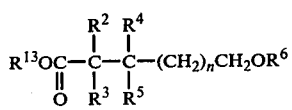

XXXVII (wherein $R^2$, $R^3$, $R^4$, $R^5$, $R^6$ and n are as hereinbefore defined, and $R^{13}$ represents a lower alkyl group preferably containing from 1 to 4 carbon atoms) with the appropriate di-lower alkyl α-lithiomethylphosphonate in an inert organic solvent, e.g. tetrahydrofuran, at a low temperature, e.g. from −78° to −50° C.

Compounds of general formula XXXVII, wherein the various symbols are as hereinbefore defined, may be prepared by reacting a compound of the general formula:

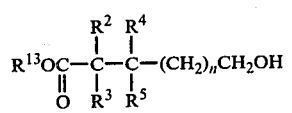

XXXVIII (wherein the various symbols are as hereinbefore defined) with a dihydropyran, dihydrofuran or ethyl vinyl ether in an inert organic solvent, e.g. methylene chloride, in the presence of a condensing agent, e.g. p-toluenesulphonic acid.

Compounds of general formula XXXVIII may be prepared by the esterification, by methods known per se for the esterification of the carboxylic acid group of a hydroxyalkylcarboxylic acid, of a compound of the general formula:

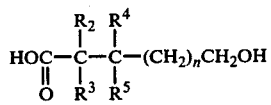

XXXIX wherein the various symbols are as hereinbefore defined.

The compounds of general formula XXXIX may be used in racemic or optically active form in the preparation of compounds of general formula XXXVIII. Suitable compounds of general formula XXXIX, which may be utilised according to the present invention, include 4-hydroxy-n-butanoic acid, 5-hydroxy-n-pentanoic acid, 6-hydroxy-n-hexanoic acid, 6-hydroxy-2-methyl-n-hexanoic acid, 6-hydroxy-2-ethyl-n-hexanoic acid, 6-hydroxy-2,2-dimethyl-n-hexanoic acid, 6-hydroxy-3-methyl-n-hexanoic acid, 6-hydroxy-3-ethyl-n-hexanoic acid and 7-hydroxy-n-heptanoic acid.

The compounds of general formula XXXIX may be prepared by methods known per se for the preparation of hydroxyalkylcarboxylic acids. For example, 6-hydroxy-2-methyl-n-hexanoic acid may be prepared by the series of reactions depicted schematically below in Scheme E:

SCHEME C

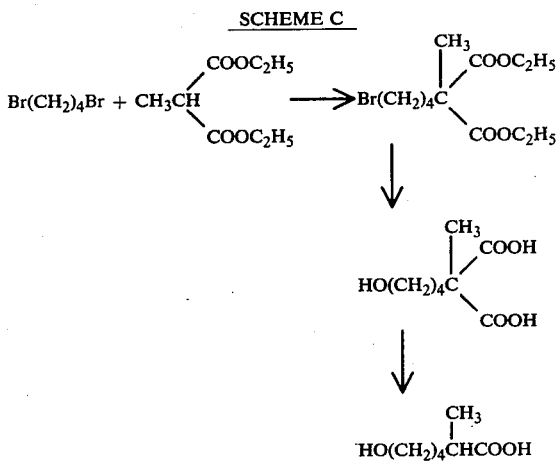

The various reaction steps depicted in Scheme E may be effected by methods known per se.

Esters of compounds of general formula VII, i.e. compounds of general formula VII wherein R represents a straight- or branched-chain alkyl group containing from 1 to 12 carbon atoms and the various other symbols are as hereinbefore defined, may be obtained by reaction of the corresponding acids of general formula VII wherein R represents a hydrogen atom with (i) the appropriate diazoalkane in a suitable inert solvent, e.g. diethyl ether, (ii) the appropriate alcohol or thiol in the presence of dicyclohexylcarbodiimide as condensing agent, or (iii) the appropriate alcohol following the formation of a mixed acid anhydride by adding a tertiary amine and then a pivaloyl halide or an arylsulphonyl or alkylsulphonyl halide (cf. our British Pat. Nos. 1362956 and 1364125). Esters of dihydro-prostaglandins of formula VII, e.g. methyl esters, may also be prepared by reduction of esters of corresponding $PG_1$ compounds conforming to that formula.

Salts may be prepared from the compounds of general formula VII, wherein R represents a hydrogen atom, by methods known per se, for example by reaction of stoichiometric quantities of compounds of general formula VII wherein R represents a hydrogen atom and the appropriate base, e.g. an alkali metal hydroxide or carbonate, ammonium hydroxide, ammonia or an amine, in a suitable solvent. The salts may be isolated by concentration of the solution or, if sufficiently insoluble in the reaction medium, by filtration, if necessary after removal of part of the solvent. Preferably the salts are non-toxic salts, i.e. salts the cations of which are relatively innocuous to the animal organism when used in therapeutic doses so that the beneficial pharmacological properties of the cyclopentane compounds of general formula VII are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms, e.g. triethanolamine.

The prostaglandin acids and esters of general formula VII may, if desired, be converted into cyclodextrin clathrates. The clathrates may be prepared by dissolving the cyclodextrin in water and/or an organic solvent which is miscible with water and adding to the solution the prostaglandin compound in a water-miscible organic solvent. The mixture is then heated and the desired cyclodextrin clathrate product isolated by concentrating the mixture under reduced pressure or by cooling and separating the product by filtration or decanting. The ratio of organic solvent to water may be varied according to the solubilities of the starting materials and products. Preferably the temperature is not allowed to exceed 70° C. during the preparation of the cyclodextrin clathrates. $\alpha,\beta$ or $\gamma$-Cyclodextrins or mixtures thereof may be used in the preparation of the cyclodextrin clathrates. Conversion into their cyclodextrin clathrates serves to increase the stability of the prostaglandin analogous compounds.

The prostaglandin analogues of general formula VII and the cyclodextrin clathrates and, when R in formula VII represents a hydrogen atom, their non-toxic salts, possess the valuable pharmacological properties typical of prostaglandins in a selective fashion including, in particular, hypotensive activity, inhibitory activity on gastric acid secretion and gastric ulceration, stimulatory activity on uterine contraction, inhibitory activity on blood platelet aggregation, bronchodilator activity and luteolytic activity at doses which do not induce, in general, diarrhoea as an undesired side-effect, and are useful in the treatment of hypertension, in the treatment of gastric ulceration, in the induction of labour in pregnant female mammals, in the treatment of disorders of the peripheral circulation, in the prevention and treatment of cerebral thrombosis and myocardial infarction, in the treatment of asthma and in the control of oestrus in female mammals. For example, in standard laboratory screening tests, (1) by intravenous administration to the allobarbital-anaesthetized dog, 20-hydroxy-$PGE_2$ produces falls in blood pressure of 18 mm.Hg and 50 mm.Hg respectively lasting 4 minutes and 14 minutes respectively at doses of 20 and 50 µg./kg. animal body weight respectively, 16($\xi$)-methyl-20-hydroxy-$PGE_1$ produces falls in blood pressure of 12 mm.Hg, 38 mm.Hg and 52 mm.Hg. respectively, lasting 3 minutes, 12 minutes and 19 minutes, respectively, at doses of 0.2, 0.5 and 1.0 µg./kg. animal body weight, respectively, 16($\xi$)-methyl-20-hydroxy-$PGE_2$ produces falls in blood pressure of 14 mm.Hg and 36 mm.Hg, respectively, lasting 23 minutes and 54 minutes, respectively, at doses of 2.0 and 10.0 µg./kg. animal body weight, respectively, 20-hydroxy-13,14-dihydro-$PGE_1$ produces falls in blood pressure of 22 mm.Hg and 40 mm.Hg, respectively, lasting 12 minutes and 24 minutes, respectively, at doses of 5.0 and 10.0 µg./kg. animal body weight, respectively, and 20-hydroxy-$PGE_1$ produces falls in blood pressure of 14 mm.Hg and 28 mm.Hg, respectively, each lasting 5 minutes at doses, respectively, of 2.0 and 5.0 µg./kg. animal body weight, respectively; (2)(a) in stress ulceration of rats produced according to the method of Takagi and Okabe [Jap. J. Pharmac, 18, 9–18, (1968)], by oral administration, 20-hydroxy-$PGE_2$ produces 56.12% and 60.25% inhibitions, respectively, of stress ulceration at doses of 1.0 and 2.0 mg./kg. animal body weight, respectively, 16($\xi$)-methyl-20-hydroxy-$PGE_1$ produces 68.87% and 78.85% inhibitions, respectively, of stress ulceration at doses of 0.1 and 0.2 mg./kg. animal body weight, respectively, and 20-hydroxy-13,14-dihydro-$PGE_1$ produces 42.14% and 47.13% inhibitions, respectively, of stress ulceration at doses of 1.0 and 2.0 mg./kg. animal body weight, respectively; (b) against gastric ulceration in rats induced by the subcutaneous administration of indomethacin, the oral administration of 20-hydroxy-$PGE_2$ and 20-hydroxy-$PGE_1$ produce inhibitions of 32% and 41%, respectively, at a dose of 100 µg./kg. animal body weight; (3) oral perfusion of 20-hydroxy-$PGE_2$ at a dose of 20 µg./kg. animal body weight/minute for 1 hour (total dose 1200 µg./kg. animal body weight) produces 35% inhibition of gastric acid secretion in male Wistar rats in which gastric acid secretion has been stimulated by the intravenous infusion of pentagastrin at a dose of 100 ng./kg. animal body weight/minute; (4) 20-hydroxy-$PGE_2$ stimulates uterine contraction in the pregnant rat at doses of 10–15 µg./kg. animal body weight by intravenous administration; (5) against adenosine diphosphate-induced blood platelet aggregation in platelet-rich plasma of rats, 16($\xi$)-methyl-20-hydroxy-$PGE_1$ produces 50% inhibition of aggregation at a concentration of $9.0 \times 10^{-2}$ µg./ml. and 20-hydroxy-13,14-dihydro-$PGE_1$ produces 50% inhibition of aggregation at a concentration of $7.0 \times 10^{-1}$ µg./ml.; (6) on guinea pig isolated tracheal muscle 20-hydroxy-$PGE_1$ produces 50% relaxation of histamine-induced contraction of 4 out of 7 preparations at the dose of $10^{-6.28}$ g./ml., 20-hydroxy-$PGE_2$ produces 50% relaxation of contraction of 5 out of 6 preparations at the dose of $10^{-6.02}$ g./ml. and 16($\xi$)-methyl-20-hydroxy-$PGE_1$ methyl ester produces 50% relaxation of contraction of 5 out of 5 preparations at the dose of $10^{-5.09}$ g./ml. (7) by intravenous administration, in anaesthetized guinea pigs in which an increase in resistance in the respiratory tract was induced by the administration of histamine, as determined by the method of Konzett and Rossler [Arch. exp. Path. Pharmak; 195, 71–74, (1940)], 20-hydroxy-PGE$_1$ produces inhibitions of the histamine induces bronchoconstriction of 68% and 88%, respectively, at doses of 0.1 and 0.5 μg./kg. animal body weight, respectively; (8) by inhalation in an aerosol, convulsions induced by the inhalation of a histamine-containing aerosol in the conscious guinea pig are delayed by 16(ξ)-methyl-20-hydroxy-PGE$_1$ leading to increases in the preconvulsion time of 81%, 130% and 143%, respectively, at doses of 1.0, 3.0 and 10.0 μg./ml. of aerosol, respectively; likewise 20-hydroxy-13,14-dihydro-PGE$_1$ increases the preconvulsion time by 106% and 161%, respectively, at doses of 10.0 and 100 μg./ml. of aerosol, respectively, 16(ξ)-methyl-20-hydroxy-PGE$_2$ increases the preconvulsion time by 39%, 88%, 129% and 162%, respectively, at doses of 1.0, 3.0, 10.0 and 30.0 μg./ml. of aerosol, respectively, 16(ξ)-methyl-20-hydroxy-PGE$_1$ methyl ester increases the preconvulsion time by 76%, 119% and 191%, respectively, at doses of 3.0, 10.0 and 30.0 μg./ml. of aerosol, respectively, and 16(ξ)-methyl-20-hydroxy-PGE$_1$ triethanolamine salt increases the preconvulsion time by 71%, 161% and 161%, respectively, at doses of 3.0, 10.0 and 30.0μg./ml. of aerosol, respectively; (9) by oral administration, against convulsions, induced by the inhalation of a histamine-containing aerosol by the conscious guinea pig, 16(ξ)-methyl-20-hydroxy-PGE$_1$ increases the preconvulsion time by 92%, 111% and 276%, respectively, at doses of 10.0, 30.0 and 100 μg./kg. animal body weight, respectively, and increases the preconvulsion time by 100% at a dose of 15.5 μg./kg. animal body weight; (10) by subcutaneous administration to the pregnant hamster on the 4th day of pregnancy, 20-hydroxy-PGF$_{2\alpha}$ and 20-hydroxy-15-epi-PGF$_{2\alpha}$ induce abortion in 50% of the animals at doses of 200 and 330 μg./kg. animal body weight, respectively; (11) the doses of 20-hydroxy-PGE$_2$ and 20-hydroxy-PGE$_1$ which produce diarrhoea in 50% of mice (ED$_{50}$) by oral administration are, respectively, 12.4 and 19.5 mg./kg. animal body weight; and (12) by oral administration to the morphine-constipated mouse, 20-hydroxy-PGE$_2$, 20-hydroxy-PGE$_1$ and 20-hydroxy-13,14-dihydro-PGE$_1$ induce the production of faeces at doses of ≈ 1000, 1000 and 1000 μg./kg. animal body weight, respectively, 20-hydroxy-PGF$_{2\alpha}$ induces a 13% production of faeces at a dose of 1000 μg./kg. animal body weight and 20-hydroxy-15-epi-PGF$_{2\alpha}$ dose not induce the production of faeces at a dose of 1000 μg./kg. animal body weight.

Preferred compounds of the invention are those compounds of general formula VII wherein R represents a hydrogen atom or a methyl group, and especially those such compounds wherein n represents 2, and more particularly those such compounds wherein one of the symbols $R^1$, $R^2$, $R^3$, $R^4$ and $R^5$ represents a hydrogen atom or a methyl group and the other symbols represent hydrogen atoms, and more especially those such compounds wherein $R^1$ represents a hydrogen atom, $R^2$ represents a hydrogen atom or a methyl group, and $R^3$, $R^4$ and $R^5$ represent hydrogen atoms, such as 20-hydroxy-PGF$_{2\alpha}$, 20-hydroxy-PGE$_2$, 20-hydroxy-PGA$_2$, 20-hydroxy-PGE$_1$, 20-hydroxy-13,14-dihydro-PGE$_1$, 16(ξ)-methyl-20-hydroxy-PGF$_{2\alpha}$, 16(ξ)-methyl-20-hydroxy-PGE$_2$, 16(ξ)-methyl-20-hydroxy-PGE$_1$ and 16(ξ)-methyl-20-hydroxy-13,14-dihydro-PGE$_1$, and methyl esters and non-toxic salts thereof.

The following Reference Examples and Examples illustrate the process of the present invention and products thereof. In the Examples, 'IR', 'NMR' and 'TLC' represent, respectively, 'Infrared absorption spectrum', 'Nuclear magnetic resonance spectrum' and 'Thin layer chromatography'.

REFERENCE EXAMPLE 1

Ethyl 6-(2-tetrahydropyranyloxy)hexanoate 66 g. (0.412 mol) of ethyl 6-hydroxyhexanoate [(prepared as described by S. R. Sandler and W. Karo, in 'Organic Functional Group Preparation', Academic Press, New York and London, vol. 1, page 262. (cf. G. B. Hatch and H. Adkins, J. Am. Chem. Soc., 59 1694 (1937))] were dissolved in 400 ml. of methylene chloride, and the mixture was reacted with 45 g. of dihydropyran and 1 g. of p-toluenesulphonic acid at 25° C. for 20 minutes. The reaction mixture was washed with an aqueous sodium bicarbonate solution, dried and concentrated. The residue was distilled in vacuo to obtain 77 g. of the title compound having the following physical characteristics:

b.p.; 135° C./3mm.Hg;

IR (liquid film); ν: 2940, 2860, 1740, 1445, 1370, 1350, 1325, 1260, 1160, 1140, 1120, 1080, 1040, 985, 910, 870 and 820 cm$^{-1}$;

NMR (CDCl$_3$ solution); δ: 4.70–4.35 (1H, m), 4.05 (2H, q), 4.00–3.00 (4H, m), 2.24 (2H, t), 1.20 (3H, t).

REFERENCE EXAMPLE 2

Dimethyl 2-oxo-7-(2-tetrahydropyranyloxy)heptylphosphonate 45 g. (0.36 mol) of dimethyl methyl phosphonate were dissolved in 400 ml. of absolute tetrahydrofuran and 180 ml. of a solution of 2N butyllithium in diethyl ether (0.36 mol) were added dropwise while maintaining the temperature below −50° C. Ten minutes later, 37 g. (0.15 mol) of ethyl 6-(2-tetrahydropyranyloxy)-hexanoate (prepared as described in Reference Example 1) in 100 ml. of absolute tetrahydrofuran were added dropwise to the solution, and the reaction mixture stirred at the same temperature for 3 hours and then for 16 hours at 0° C.

The reaction mixture was acidified with acetic acid and evaporated. The residue was dissolved in a small amount of water and extracted with diethyl ether. The extracts were dried over MgSO$_4$ and concentrated. The residue was distilled at 140° C. (oil bath temperature) at a pressure of 0.2 mm.Hg. The residue was 31 g. of the title compound, the boiling point of which was too high to permit distillation and which had the following physical characteristics:

IR (liquid film); ν: 2950, 2870, 1720, 1455, 1445, 1410, 1375, 1365, 1335, 1275, 1200, 1190, 1140, 1120, 1110–990, 920, 880 and 820 cm$^{-1}$;

NMR (CDCl$_3$ solution); δ: 4.75–4.30 (1H, m), 4.15–3.10 (4H, m), 3.75 (6H, d), 3.06 (2H, d), 2.58 (2H, t).

REFERENCE EXAMPLE 3

Methyl 9α-acetoxy-11α-(2-tetrahydropyranyloxy)-15-oxo-20-(2-tetrahydropyranyloxy)prosta-cis-5, trans-13-dienoate.

1.44 g. of sodium hydride (55% content) were suspended in 200 ml. of absolute tetrahydrofuran. With stirring under an atmosphere of nitrogen at room temperature, 11.3 g. (0.035 mol) of dimethyl 2-oxo-7-(2-tetrahydropyranyloxy)heptylphosphonate (prepared as described in Reference Example 2) in 100 ml. of tetrahydrofuran were added to the solution, and stirred for 20 minutes.

11.6 g. (0.0294 mol) of 1α-acetoxy-2α-(6-methoxycarbonylhex-cis-2-enyl)-3β-formyl-4α-(2-tetrahydropyranyloxy)-cyclopentane in 50 ml. of tetrahydrofuran were added and stirred for 1 hour at room temperature. The reaction mixture was then neutralised with acetic acid, filtered and the filtrate concentrated. The residue was purified by column chromatography on silica gel using benzene:ethyl acetate (4:1) as eluent to give 16.0 g. of the title compound having the following physical characteristics:

IR (liquid film); ν: 2950, 2870, 1745, 1700, 1675, 1635, 1455, 1445, 1380, 1360, 1330, 1255, 1200, 1190–1155, 1145, 1130, 1085, 1045, 980, 925, 915, 880, 855 and 825 $cm^{-1}$;

NMR ($CDCl_3$ solution); δ: 6.65 (1H, q), 6.15 (1H, d), 5.60–5.15 (2H, m), 5.15–4.85 (1H, m), 4.80–4.35 (2H, m), 4.30–3.00 (6H, m), 3.62 (3H, s), 2.04 (3H, s);

TLC (developing solvent benzene:ethyl acetate = 2:1): Rf = 0.54.

1α-Acetoxy-2α-6-methoxycarbonylhex-cis-2-enyl)-3β-formyl-4α-(2-tetrahydropyranyloxy)-cyclopentane, used as a starting material in the procedure described above, was prepared from 2-oxa-3-oxo-6-syn-hydroxymethyl-7-antiacetoxy-cis-bicyclo[3,3,0]-octane, (which may be prepared as described by E. J. Corey et al, J. Am. Chem. Soc., 91, 5675, (1969) and ibid., 92 397, (1970)), as follows:

190 g. of 2-oxa-3-oxo-6-syn-hydroxymethyl-7-anti-acetoxy-cis-bicyclo[3,3,0]octane in 1.5 liters of absolute methanol and 130 g. of potassium carbonate were stirred at room temperature for 1 hour, successively cooled in an ice-bath and neutralised with hydrochloric acid. The precipitate was filtered off and the filtrate was concentrated under reduced pressure. The residue was washed with ethanol, followed by ethyl acetate, and completely dried to give 124 g. of 2-oxa-3-oxo-6-syn-hydroxymethyl-7-anti-hydroxy-cis-bicyclo[3,3,0]octane as white crystallites having the following physical characteristics:
m.p. 119° C.;

IR (KBr tablet); ν: 3350, 2970–2880, 1740, 1480, 1440, 1410, 1380, 1335, 1305, 1270, 1205, 1100, 1080, 1060, 1040, 1020, 1000 and 975 $cm^{-1}$;

NMR ($CDCl_3$ + deutero dimethylsulphoxide solution); δ: 5.10–4.60 (1H, m), 4.29 (2H, s), 4.13–3.77 (1H, m), 3.38 (2H, d);

TLC (developing solvent methylene chloride:methanol = 20:1): Rf = 0.27.

124 g. of 2-oxa-3-oxo-6-syn-hydroxymethyl-7-anti-hydroxy-cis-bicyclo[3,3,0]octane prepared as described above were dissoled in absolute pyridine (1.4 liters) and cooled to −40° C. 74 g. of acetic anhydride were then added dropwise and stirred for 5 hours at −40° to −20° C. and then for 16 hours at 0° C. The pyridine was removed under reduced pressure, the residue was dissolved in 1 liter of ethyl acetate, stirred vigorously with 200 g. of sodium bisulphate, filtered and the filtrate concentrated under reduced pressure. The residue was purified by column chromatography on silica gel using benzene-ethyl acetate (1:3) as eluent to give 112 g. of 2-oxa-3-oxo-6-syn-acetoxymethyl-7-anti-hydroxy-cis-bicyclo[3,3,0]octane as colourless needles having the following physical characteristics:
m.p. 36° to 37° C.;

IR (KBr tablet); ν: 3450, 2960, 2850, 1775, 1740, 1420, 1370, 1250, 1190, 1120, 1090, 1040, and 980 $cm^{-1}$;

NMR ($CDCl_3$ solution); δ: 5.15–4.6 (1H, m), 4.3–3.75 (3H, m), 3.50 (1H, s), 2.02 (3H, s);

TLC (developing solvent methylene chloride:methanol = 20:1): Rf = 0.50.

43 g. of 2-oxa-3-oxo-6-syn-acetoxymethyl-7-anti-hydroxy-cis-bicyclo[3,3,0]octane prepared as described above were dissolved in 520 ml. of methylene chloride and stirred with 25 g. of dihydropyran and 0.52 g. of p-toluenesulphonic acid for 20 minutes at room temperature. The reaction mixture was neutralised with an aqueous solution of sodium bicarbonate, diluted with ethyl acetate, washed with water, dried and concentrated under reduced pressure to give 2-oxa-3-oxo-6-syn-acetoxymethyl-7-anti-(2-tetrahydropyranyloxy)-cis-bicyclo[3,3,0]octane (56 g.) as a colourless oil having the following physical characteristics:

IR (liquid film); ν: 2950–2840, 1775, 1740, 1465, 1440, 1390–1340, 1240, 1180, 1140–1120, 1080, 1040 and 980 $cm^{-1}$;

NMR ($CDCl_3$ solution); δ: 5.2–4.72 (1H, m), 4.72–4.30 (1H, m), 4.2–3.2 (5H, m), 2.01 (3H, s);

TLC (developing solvent methylene chloride:methanol = 20:1): Rf = 0.74. 56 g. of 2-oxa-3-oxo-6-syn-acetoxymethyl-7-anti-(2-tetrahydropyranyloxy)-cis-bicyclo[3,3,0]octane prepared as described above were dissolved in 900 ml. of toluene and cooled to −60° C. To the solution, 456 ml. of a 25% (w/v) solution of diisobutylaluminium hydride in toluene was added and stirred for 20 minutes. Methanol was then added to decompose excess diisobutylaluminium hydride together with water. The precipitate was filtered off and the filtrate dried and concentrated under reduced pressure to give 35.2 g. of 2-oxa-3-hydroxy-6-syn-hydroxymethyl-7-anti-(2-tetrahydropyranyloxy)-cis-bicyclo[3,3,0]octane as a colourless oil having the following physical characteristics:

IR (liquid film); ν: 3400, 2940–2860, 1465–1440, 1380, 1355, 1325, 1260, 1200, 1140, 1120, 1075 and 1020 $cm^{-1}$;

TLC (developing solvent ethyl acetate): Rf = 0.25.

37.6 g. of sodium hydride (63.5% content) were suspended in 400 ml. of dimethylsulphoxide and stirred with heating at 70° C., for 1.5 hours to obtain sodiomethylsulphinylcarbanide. The reaction mixture was allowed to cool to room temperature and then added dropwise to a solution of 226 g. of 4-carboxy-n-butyl-triphenylphosphonium bromide in 460 ml. of dimethylsulphoxide, the reaction temperature being kept within the range of 20° to 25° C.

A solution of 35.2 g. of 2-oxa-3-hydroxy-6-syn-hydroxymethyl-7-anti-(2-tetrahydropyranyloxy)-cis-bicyclo[3,3,0]octane prepared as described above in 90 ml. of dimethylsulphoxide was added, and the mixture stirred vigorously at 35° to 40° C. for 1.5 hours. The reaction mixture was poured into 6 liters of ice-water and neutral substance was removed by extraction with a mixture of ethyl acetate and diethyl ether (1:1). The aqueous layer was acidified to pH 2 with a saturated solution of oxalic acid and extracted with a mixture of diethyl ether and n-pentane (1:1). The extracts, after washing with water, were dried over sodium sulphate and concentrated under reduced pressure. The residue was subjected to column chromatography on silica gel using benzene-methanol (10:1) as eluent to give 35 g. of 2α-(6-carboxyhex-cis-2-enyl)-3β-hydroxymethyl-4α-(2-tetrahydropyranyloxy)cyclopentan-1α-ol as a colourless oil having the following physical characteristics:

IR (liquid film); ν: 3400, 2940–2860, –2300, 1710, 1450, 1435, 1400, 1355, 1245, 1200, 1140, 1120, 1075 and 1025 cm$^{-1}$;

NMR (CDCl$_3$ solution); δ: 6.20 (3H, s), 5.50–5.10 (2H, m), 4.75–4.36 (1H, m), 4.24–3.85 (2H, m), 3.85–3.0 (4H, m);

TLC (developing solvent chloroform-tetrahydrofuran-acetic acid = 10:2:1): Rf = 0.53.

To 18.8 g. of 2α-(6-carboxyhex-cis-2-enyl)3β-hydroxymethyl-4α-(2-tetrahydropyranyloxy)-cyclopentan-1α-ol prepared as described above in 130 ml. of diethyl ether, an ethereal solution of newly prepared diazomethane was added, with cooling in an ice-bath, until the solution showed a pale yellow colour. The reaction mixture was concentrated in vacuo and the residue was subjected to column chromatography on silica gel using cyclohexane-ethyl acetate (2:1) as eluent to give 15.4 g. of 2α-(6-methoxycarbonylhex-cis-2-enyl)-3β-hydroxymethyl-4α-(2-tetrahydropyranyloxy)cyclopentan-1α-ol as a colourless oil having the following physical characteristics:

IR (liquid film); ν: 3450, 2950–2870, 1740, 1440, 1360, 1325, 1250, 1200, 1140, 1120, 1080 and 1025 cm$^{-1}$;

NMR (CDCl$_3$ solution); δ: 5.55–5.00 (2H, m), 4.78–4.30 (1H, m), 4.20–3.06 (6H, m), 3.55 (3H, s), 2.97 (2H, s);

TLC (developing solvent methylene chloride:methanol = 19:1): Rf = 0.43.

13.1 g. of 2α-(6-methoxycarbonylhex-cis-2-enyl)-3β-hydroxymethyl-4α-(2-tetrahydropyranyloxy)-cyclopentan-1α-ol prepared as described above were dissolved in 250 ml. of absolute methylene chloride, 25 ml. of pyridine were added to the solution and the atmosphere was replaced by nitrogen gas with cooling to −20° C. While being kept stirred, 5.1 ml. of trimethylchlorosilane in 30 ml. of methylene chloride were added to the solution dropwise and stirring was continued for 30 minutes at the same temperature. A sample was then subjected to TLC and the following Rf value was obtained:

TLC (developing solvent benzene:ethyl acetate = 2:1): Rf = 0.61.

To the reaction mixture, 2.9 ml. of acetyl chloride in 20 ml. of methylene chloride were added dropwise and stirred for 30 minutes at room temperature. 2 ml. of ethanol were then added to decompose the excess acetyl chloride. To the reaction mixture, 50 g. of sodium bisulphate were added to remove pyridine, and the resulting precipitate was filtered off. The filtrate was concentrated under reduced pressure. A sample was subjected to TLC and the following Rf value was obtained:

TLC (developing solvent benzene:ethyl acetate = 2:1): Rf = 0.82.

The residue was diluted with ethyl acetate (300 ml.) and stirred vigorously with 100 ml. of an aqueous solution of oxalic acid at room temperature. The organic layer was separated and washed successively with water, an aqueous solution of sodium bicarbonate, water and brine, dried with sodium sulphate and concentrated under reduced pressure to give 13.7 g. of the crude product. The crude product was subjected to column chromatography on silica gel using benzene-ethyl acetate (3:1) as eluent to give 7.45 g. of 1α-acetoxy-2α-(6-methoxycarbonylhex-cis-2-enyl)-3β-hydroxymethyl-4α-(2-tetrahydropyranyloxy)-cyclopentane, 2.40 g. of 1α-hydroxy-2α-(6-methoxycarbonylhex-cis-2-enyl)-3β-hydroxymethyl-4α-(2-tetrahydropyranyloxy)-cyclopentane, 720 mg. of 1α-hydroxy-2α-(6-methoxycarbonylhex-cis-2-enyl)-3β-acetoxymethyl-4α-(2-tetrahydropyranyloxy)-cyclopentane, and 1.45 g. of 1α-acetoxy-2α-(6-methoxycarbonylhex-cis-2-enyl)-3β-acetoxymethyl-4α-(2-tetrahydropyranyloxy)-cyclopentane. 1α-Acetoxy-2α-(6-methoxycarbonylhex-cis-2-enyl)-3β-hydroxymethyl-4α-(2-tetrahydropyranyloxy)-cyclopentane had the following physical characteristics:

IR (liquid film); ν: 3450, 3000, 2950, 2870, 1740, 1440, 1380, 1330, 1250, 1200, 1160, 1140, 1080, 1030, 980, 920, 875 and 815 cm$^{-1}$;

NMR (CDCl$_3$ solution); δ: 5.45–5.27 (2H, m), 5.16–4.92 (1H, m), 4.76–4.46 (1H, m), 4.27–3.96 (1H, m), 3.67 (3H, s), 2.98–2.64 (1H, m), 2.05 (3H, s);

TLC (developing solvent benzene:ethyl acetate = 2:1): Rf = 0.27.

Under an atmosphere of nitrogen and at laboratory temperature, 80 ml. of absolute methylene chloride and 4.4 ml. of absolute pyridine were stirred with 2.88 g. of chrominum trioxide for 15 minutes. 12 g. of infusorial earth were then added to the solution. 956 mg. of 1α-acetoxy-2α-(6-methoxycarbonylhex-cis-2-enyl)3β-hydroxymethyl-4α-(2-tetrahydropyranyloxy)-cyclopentane (prepared as described above) in 20 ml. of methylene chloride were then added and stirred for 10 minutes at laboratory temperature. The reaction mixture was then treated with 20 g. of sodium bisulphate and stirred for a further 10 minutes at laboratory temperature and filtered. The filtrate was then concentrated under reduced pressure at laboratory temperature.

The residue was subjected to column chromatography on silica gel using benzene:ethyl acetate (5:1) as eluent to give 768 mg. of 1α-acetoxy-2α-(6-methoxycarbonylhex-cis-2-enyl)-3β-formyl-4α-(2-tetrahydropyranyloxy-cyclopentane as a colourless oil having the following physical characteristics:

IR (liquid film); ν: 3000, 2950, 2860, 2725, 1740, 1440, 1380, 1325, 1255, 1200, 1165, 1140, 1085, 1030, 980, 920, 880 and 820 cm$^{-1}$;

NMR (CDCl$_3$ solution); δ: 9.85–9.68 (1H, m), 5.45–4.96 (1H, m), 4.68–4.48 (1H, m), 4.48–4.25 (1H, m), 3.67 (3H, s), 2.08 (3H, s);

TLC (developing solvent benzene:ethyl acetate = 2:1): Rf = 0.66.

REFERENCE EXAMPLE 4

Methyl 9α-acetoxy-11α,20-bis-(2-tetrahydropyranyloxy)-15α-hydroxyprosta-cis-5,trans-13-dienoate and methyl 9α-acetoxy-11α,20-bis-(2-tetrahydropyranyloxy)-15β-hydroxyprosta-cis-5,trans-13-dienoate.

A solution of 12.3 g. of methyl 9α-acetoxy-11α-(2-tetrahydropyranyloxy)-15-oxo-20-(2-tetrahydropyranyloxy)-prosta-cis-5,trans-13-dienoate (prepared as described in Reference Example 3) in 200 ml.

of methanol was cooled to −30° to −40° C. with stirring. 2.7 g. of sodium borohydride were added in portions. The reaction mixture was then stirred for 30 minutes at the same temperature and then neutralised with acetic acid. The solvent was removed and the residue was extracted with ethyl acetate. The extracts were washed with an aqueous solution of sodium bicarbonate, dried with magnesium sulphate, and concentrated. The residue was subjected to column chromatography on silica gel using benzene-ethyl acetate as eluent to give 4.89 g. of α-OH title compound, 4.34 g. of β-OH title compound and 2.78 g. of a mixture of the α-OH and β-OH title compounds. TLC of the α-OH and β-OH title compounds gave the following results:

TLC (developing solvent benzene-ethyl acetate = 1:1):
Rf = 0.53 (α-OH title compound)
Rf = 0.62 (β-OH title compound)

Identification of α-OH or β-OH title compounds was done by testing the biological activities of 20-hydroxy-$PGF_{2\alpha}$ which had been synthesised from both hydroxy compounds showing different Rf values. The α-OH and β-OH title compounds had the following other physical characteristics:

IR (liquid film); ν: 3450, 2940, 2860, 1740, 1455, 1445, 1380, 1360, 1330, 1250, 1200, 1140, 1125, 1080, 1035, 980, 925, 910, 875 and 820 cm$^{-1}$;

NMR ($CDCl_3$ solution); δ: 5.65–5.40 (2H, m), 5.40–5.10 (2H, m), 5.10–4.80 (1H, m), 4.73–4.30 (2H, m), 4.30–3.00 (8H, m), 3.56 (3H, s), 2.01 (3H, s).

REFERENCE EXAMPLE 5

Methyl 9α-acetoxy-11α,15α,20-tri-(2-tetrahydropyranyloxy)-prosta-cis-5-trans-13-dienoate.

4.27 g. of methyl 9α-acetoxy-11α,20-bis-(2-tetrahydropyranyloxy)-15α-hydroxyprosta-cis-5,trans-13-dienoate (prepared as described in Reference Example 4) were dissolved in 40 ml. of methylene chloride, and the mixture was reacted with 1.1 ml. of dihydropyran and 20 mg. of p-toluenesulphonic acid at 25° C. for 30 minutes to give 4.9 g. of title compound having the following physical characteristics:

IR (liquid film); ν: 2950, 2870, 1745, 1460, 1445, 1380, 1360, 1335, 1250, 1200, 1190, 1165, 1140, 1080, 1045, 1030, 980, 925, 915, 880 and 825 cm$^{-1}$;

NMR ($CDCl_3$ solution); δ: 5.65–5.10 (4H, m), 5.10–4.80 (1H, m), 4.80–4.35 (3H, m), 4.20–3.00 (10H, m), 3.58 (3H, s), 2.00 (3H, s).

TLC (developing solvent benzene-ethyl acetate = 1:1): Rf = 0.80.

EXAMPLE 1

9α-Hydroxy-11α,15α,20-tri-(2-tetrahydropyranyloxy)-prosta-cis-5trans,-13-dienoic acid 4.9 g. of methyl 9α-acetoxy-11α,15α,20-tri-(2-tetrahydropyranyloxy)-prosta-cis-5,trans-13-dienoate (prepared as described in Reference Example 5) were added to a mixture of 3 g. of potassium hydroxide, 5 ml. of water and 20 ml. of methanol and stirred at room temperature for 2 hours. The reaction mixture was then neutralised with oxalic acid, extracted with ethyl acetate, washed with water, dried with magnesium sulphate and concentrated. The residue was subjected to column chromatography on silica gel using benzene-ethyl acetate (1:2) as eluent to give 3.6 g. of the title compound having the following physical characteristics:

IR (liquid film); ν: 3450, 2940, 2860–2350, 1745, 1715, 1455, 1445, 1380, 1360, 1330, 1250, 1200, 1190, 1140, 1125, 1080, 1040, 1030, 980, 915, 890, 875 and 820 cm$^{-1}$;

NMR ($CDCl_3$ solution); δ: 6.50 (2H, broad s), 4.85–4.35 (4H, m), 4.30–3.00 (11H, m);

TLC (developing solvent benzene-ethyl acetate = 1:2): Rf = 0.12.

EXAMPLE 2

20-Hydroxy-$PGF_{2\alpha}$ 686 mg. of 9α-hydroxy-11α,15α,20-tri-(2-tetrahydropyranyloxy)-prosta-cis-5,trans-13-dienoic acid (prepared as described in Example 1) were dissolved in 11 ml. of a mixture of acetic acid, water and tetrahydrofuran (65:35:10), and the resulting solution was stirred vigorously at 40° C. for 2 hours. The reaction mixture was concentrated under reduced pressure. The residue was mixed with toluene and the acetic acid removed by azeotropic distillation. After the treatment had finished, the residue was purified by column chromatography on silica gel using ethyl acetate-ethanol (30:1) as eluent, to give 300 mg. of pure 20-hydroxy-$PGF_{2\alpha}$ as a colourless oil having the following physical characteristics:

IR (liquid film); ν: 3350, 3010, 2950, 2860, -2200, 1715, 1460, 1440, 1415, 1250, 1190, 1150, 1120, 1085, 1060, 980, 935 and 890 cm$^{-1}$;

NMR ($CDCl_3$ + deutero dimethylsulphoxide solution); δ: 5.67–5.13 (4H, m), 5.10–4.32 (5H, broad s), 4.16–3.67 (3H, m), 3.51 (2H, t).

TLC (developing solvent ethyl acetate-formic acid = 400:5): Rf = 0.06.

20-Hydroxy-15-epi-$PGF_{2\alpha}$ was prepared from 9α-acetoxy-11α,20-bis-(2-tetrahydropyranyloxy)-15β-hydroxyprosta-cis-5,trans-13-dienoate (prepared as described in Reference Example 4) by procedures similar to those described in Reference Example 5 and Examples 1 and 2. The peaks of 20-hydroxy-15-epi-$PGF_{2\alpha}$ on NMR and IR were substantially the same as those of 20-hydroxy-$PGF_{2\alpha}$. The Rf value of 20-hydroxy-15-epi-$PGF_{2\alpha}$ on TLC (developing solvent ethyl acetate-formic acid = 400:5) was 0.10.

EXAMPLE 3

9-Oxo-11α,15α,20-tri-(2-tetrahydropyranyloxy)-prosta-cis-5,trans-13-dienoic acid 1.63 g. of 9α-hydroxy-11α,15α,20-tri-(2-tetrahydropyranyloxy)-prosta-cis-5,-trans-13-dienoic acid (prepared as described in Example 1) were dissolved in 25 ml. of diethyl ether. The solution was cooled to 0°–5° C. and then a solution of 1g. of chromium trioxide, 14.5 g. of manganese sulphate, 1.1 ml. of sulphuric acid and 22 ml. of water was added and the reaction mixture was stirred vigorously at 0°–5° C. for 1 hour. The reaction mixture was diluted with diethyl ether and the aqueous layer separated.

The aqueous layer was extracted with diethyl ether. The combined ethereal extracts were washed sufficiently with water until the washing was not coloured yellow, dried over sodium sulphate and then concentrated under reduced pressure. The residue was purified by chromatography on silica gel using benzene-ethyl acetate (1:1) as eluent to give 1.21 g. of the title compound having the following physical characteristics:

IR (liquid film); ν: 2940, 2860–2300, 1745, 1715, 1455, 1445, 1375, 1355, 1325, 1270, 1250, 1195, 1180, 1160, 1140, 1125, 1080, 1040, 1025, 980, 915, 875 and 820 cm$^{-1}$;

NMR (CDCl$_3$ solution); δ: 9.10 (1H, s), 5.75–5.15 (4H, m), 4.85–4.35 (3H, m), 4.30–3.10 (10H, m);

TLC (developing solvent methylene chloride-methanol = 19:1): Rf = 0.32;

Optical Rotation: [α]$_D^{21}$ = +23.95° (c = 0.91, ethanol).

EXAMPLE 4

20-Hydroxy-PGE$_2$ 1.20 g. of 9-oxo-11α,15α,20-tri-(2-tetrahydropyranyloxy)-prosta-cis-5,trans-13-dienoic acid (prepared as described in Example 3) were dissolved in 22 ml. of a mixture of acetic acid, water and tetrahydrofuran (65:35:10) and stirred at 40° C. for 1 hour. The reaction mixture was then mixed with toluene and the acetic acid removed by azeotropic distillation. The residue was purified by column chromatography on silica gel using ethyl acetate-ethanol (40:1) as eluent to give 443 mg. of the title compound as an oil having the following physical characteristics:

IR (liquid film); ν: 3370, 3020, 2940, 2860–2200, 1745, 1715, 1440, 1410, 1380, 1250, 1165, 1080, 1055, 1015, 980 and 870 cm$^{-1}$;

NMR (CDCl$_3$ + deutero dimethylsulphoxide solution); δ: 5.70–5.45 (2H, m), 5.45–5.23 (2H, m), 5.03 (4H, broad s), 4.28–3.77 (2H, m), 3.54 (2H, t);

TLC (developing solvent ethyl acetate-formic acid = 400:1): Rf = 0.20;

Optical Rotation [α]$_D^{23}$ = −66.3° (c = 0.845, ethanol).

EXAMPLE 5

20-Hydroxy-PGA$_2$ 278 mg. of 20-hydroxy-PGE$_2$ (prepared as described in Example 4) were dissolved in 20 ml. of a mixture of tetrahydrofuran and 1N hydrochloric acid (1:1) and the solution was stirred at 60° C. for 2 hours with 120 mg. of cupric chloride. The reaction mixture was then diluted with ethyl acetate, washed with water, dried with magnesium sulphate and concentrated under reduced pressure. The residue was purified by column chromatography on silica gel using cyclohexane-ethyl acetate (1:2) as eluent to obtain 174 mg. of 20-hydroxy-PGA$_2$ as an oil having the following physical characteristics:

IR (liquid film); ν: 3380, 3020, 2940, 2860–2200, 1710, 1590, 1460, 1440, 1415, 1360, 1320, 1245, 1190, 1160, 1080, 1060, 980, 880 and 825 cm$^{-1}$;

NMR (CDCl$_3$ + deutero dimethylsulphoxide solution); δ: 7.60–7.43 (1H, m), 6.23–6.07 (1H, m), 5.73–5.51 (2H, m), 5.51–5.25 (2H, m), 4.93 (3H, broad s), 4.18–3.93 (1H, m), 3.56 (2H, t), 3.35–3.11 (1H, m);

TLC (developing solvent ethyl acetate:formic acid = 400:1): Rf = 0.49;

Optical Rotation: [α]$_D^{21}$ = +156.5° (c = 0.66, ethanol).

EXAMPLE 6

9α-Hydroxy-11α,15α,20-tri-(2-tetrahydropyranyloxy)-prost-trans-13-enoic acid 1 g. of 5% palladium on charcoal was suspended in 50 ml. of methanol. Air in the apparatus was replaced with hydrogen and 1.3 g. of 9α-hydroxy-11α,15α,20-tri-(2-tetrahydropyranyloxy)-prosta-cis-5,trans-13-dienoic acid (prepared as described in Example 1) were added.

Catalytic reduction of the compound was carried out at room temperature under ambient pressure. After completion of the reaction, the catalyst was separated by filtration and the filtrate was evaporated under reduced pressure to give 1.33 g. of the title compound having the following physical characteristics:

IR (liquid film); ν: 3450, 3010, 2940, 2860–2250, 1715, 1540, 1470, 1455, 1390, 1360, 1330, 1270, 1200, 1185, 1140, 1125, 1080, 1030, 985, 915, 875 and 820 cm$^{-1}$;

NMR (CDCl$_3$ solution); δ: 6.12 (2H, s), 5.65–5.15 (2H, m), 4.85–4.35 (3H, m), 4.35–3.05 (1H, m).

In thin layer chromatography (silica gel), the product and the starting material behaved similarly. However, after hydrolysis of the product with 0.1N hydrochloric acid at 75° C. for 5 minutes followed by extraction with ethyl acetate, the result of thin layer chromatography with a plate impregnated with silver nitrate by using ethyl acetate:methanol:acetic acid (10:1:1) as developing solvent was Rf 0.27. On the other hand, if the same treatment was repeated using the said starting material, the resulting Rf was 0.15.

EXAMPLE 7

9-Oxo-11α,15α,20-tri-(2-tetrahydropyranyloxy)-prost-trans-13-enoic acid 1.33 g. of 9α-hydroxy-11α,15α,20-tri-(2-tetrahydropyranyloxy)-prost-trans-13-enoic acid (prepared as described in Example 6) were dissolved in 25 ml. of diethyl ether. The solution was cooled to 0°–5° C. and then 25 ml. of a chromic acid solution (prepared by dissolving 3.2 g. of chromium trioxide, 10.8 g. of manganese sulphate and 3.56 ml. of sulphuric acid in water to make the total volume 80 ml.) were added and the reaction mixture stirred vigorously at 0°–5° C. for 1 hour.

The reaction mixture was diluted with diethyl ether and the aqueous layer separated. The aqueous layer was extracted with diethyl ether. The combined ethereal extracts were washed sufficiently with water until the washing was not coloured yellow, dried with sodium sulphate and then concentrated under reduced pressure. The residue was subjected to column chromatography on silica gel using benzene:ethyl acetate (1:1) as eluent to give 906 mg. of the title compound as an oil having the following physical characteristics:

IR (liquid film); ν: 2940, 2860–2350, 1745, 1715, 1470, 1455, 1445, 1380, 1360, 1330, 1250, 1200, 1190, 1160, 1140, 1085, 1045, 1030, 985, 915, 875 and 820 cm$^{-1}$;

NMR (CDCl$_3$ solution); δ: 9.45 (1H, s), 5.80–5.10 (2H, m), 4.85–4.40 (3H, m), 4.40–3.05 (10H, m);

TLC (developing solvent methylene chloride:methanol = 19:1): Rf = 0.29.

EXAMPLE 8

20-Hydroxy-PGE$_1$ 906 mg. of 9-oxo-11α,15α,20-tri-(2-tetrahydropyranyloxy)-prost-trans-13-enoic acid (prepared as described in Example 7) were dissolved in 11 ml. of a mixture of acetic acid, water and tetrahydrofuran (65:35:10) and stirred at 38°–40° C. for 2 hours. The reaction mixture, to which toluene was added to remove the acetic acid by azeotropic distillation, was then concentrated in vacuo. The residue was purified by column chromatography on silica gel using ethyl acetate:ethanol (40:1) as eluent.

The eluate was concentrated to dryness and dissolved in ethyl acetate, and cyclohexane was added to the solution until it became whitely turbid, and allowed to stand at room temperature. The mother liquor was removed with decantation to obtain the title compound as white powdery crystals having the following physical characteristics: m.p. 97° to 98° C.;
IR (KBr); ν: 3470, 2940, 2850, –2150, 1740, 1715, 1465, 1415, 1370, 1330, 1285, 1255, 1230, 1185, 1110, 1080, 1035, 1010 and 985 cm$^{-1}$;
NMR (CDCl$_3$ + deutero dimethylsulphoxide solution); δ: 5.68–5.46 (2H, m), 5.98–4.22 (4H, broad s), 4.22–3.78 (2H, m), 3.54 (2H, t);
TLC (developing solvent ethyl acetate:formic acid = 400:1): Rf = 0.19;
Optical Rotation: $[\alpha]_D^{20} = -43.9°$ (c = 1.03, ethanol).

EXAMPLE 9

9α-Hydroxy-11α,15α, 20-tri-(2-tetrahydropyranyloxy)-prostanoic acid 180 mg. of platinum oxide were suspended in 30 ml. of methanol. Air in the apparatus was replaced with hydrogen and 2.02 g. of 9α-hydroxy-11α,15α,20-tri-(2-tetrahydropyranyloxy)-prosta-cis-5,trans-13-dienoic acid (prepared as described in Example 1) were added.

Catalytic reduction of the compound was carried out at room temperature under ambient pressure. After completion of the reaction, the catalyst was separated by filtration and the filtrate was evaporated under reduced pressure to give 2.00 g. of the title compound having the following physical characteristics:
NMR (CDCl$_3$ solution); δ: 4.85–4.50 (3H, m), 4.35–3.15 (11H, m);
TLC (developing solvent benzene:ethyl acetate = 1:2): Rf = 0.31.

EXAMPLE 10

9-Oxo-11α,15α,20-tri-(2-tetrahydropyranyloxy)-prostanoic acid 2.02 g. of 9α-hydroxy-11α,15α,20-tri-(2-tetrahydropyranyloxy)-prostanoic acid (prepared as described in Example 9) were dissolved in 38 ml. of diethyl ether. The solution was cooled to 0° C. to 5° C. and then 38 ml. of a chromic acid solution (prepared as described in Example 7) were added and the reaction mixture was stirred vigorously at 0° to 5° C. for one hour.

The reaction mixture was diluted with diethyl ether and the aqueous layer separated. The aqueous layer was extracted with diethyl ether. The combined ethereal layers were washed sufficiently with water until the washing was not coloured yellow, dried with sodium sulphate and then concentrated under reduced pressure. The residue was subjected to column chromatography on silica gel using a mixture of benzene and ethyl acetate (2:1) as eluent to give 1.44 g. of the title compound having the following physical characteristics:
NMR (CDCl$_3$ solution); δ: 4.85–4.50 (3H, m), 4.40–3.20 (10H, m);
TLC (developing solvent benzene:ethyl acetate = 1:2): Rf = 0.58.

EXAMPLE 11

20-Hydroxy-13,14-dihydro-PGE$_1$ 1.44 g. of 9-oxo-11α,15α,20-tri-(2-tetrahydropyranyloxy)-prostanoic acid (prepared as described in Example 10) were dissolved in 24 ml. of a mixture of acetic acid, water and tetrahydrofuran (65:35:10) and stirred at 38° to 40° C. for 1.5 hours. The reaction mixture, to which toluene was added to remove the acetic acid by azeotropic distillation, was then concentrated in vacuo. The residue was purified by column chromatography on silica gel using a mixture of ethyl acetate and ethanol (40:1) as eluent to give 350 mg. of the title compound having the following physical characteristics:
IR (liquid film); ν: 3600–2400, 1740, 1460, 1400, 1040 cm$^{-1}$;
NMR (CDCl$_3$ and acetone-d$_6$ solution): δ: 4.30–3.80 (5H, m), 3.70–3.40 (3H, m), 2.58 (1H, dd);
TLC (developing solvent ethyl acetate:formic acid = 400:5): Rf = 0.22.

REFERENCE EXAMPLE 6

Ethyl 2(ξ)-methyl-6-(2-tetrahydropyranyloxy)-hexanoate

A solution of 6.2 ml. of diisopropylamine in 50 ml. of tetrahydrofuran was cooled to −70° C., and to it 36 ml. of a solution of n-butyllithium in n-hexane (1.37 molar concentration) were added dropwise and stirred for 15 minutes at −70° C. to give lithium diisopropylamide.

To the lithium diisopropylamide solution 9.0 g. of ethyl 6-(2-tetrahydropyranyloxy)-hexanoate (prepared as described in Reference Example 1) in 20 ml. of tetrahydrofuran were added dropwise at −70° C. and the reaction mixture was stirred for 30 minutes at the same temperature. A solution of 3 ml. of methyl iodide in 20 ml. of tetrahydrofuran was added dropwise to the reaction mixture at −70° C. and stirring was continued for 10 minutes at the same temperature and then for one hour at room temperature. The reaction mixture was poured into water and extracted with ethyl acetate. The organic extracts were washed with water, dried over magnesium sulphate and concentrated under reduced pressure. The residue was distilled in vacuo to give 6.2 g. of the title compound having the following physical characteristics:
boiling point: 129° C. to 132° C./4 mm.Hg;
IR (liquid film); ν: 2920, 2850, 1735, 1460, 1380, 1355, 1265, 1205, 1080, 1040 cm$^{-1}$;
NMR (CCl$_4$ solution); δ: 4.70–4.50 (1H, m), 4.42 (2H, q), 4.40–3.15 (4H, m), 1.25 (3H, t).

REFERENCE EXAMPLE 7

Dimethyl 2-oxo-3(ξ)-methyl-7-(2-tetrahydropyranyloxy)heptylphosphonate 12 g. of dimethyl methylphosphonate were dissolved in 140 ml. of absolute tetrahydrofuran and 71 ml. of a solution of 1.37M n-butyllithium in n-hexane were added dropwise whilst maintaining the temperature below −50° C. Ten minutes later 12.4 g. of ethyl 2(ξ)-methyl-6-(2-tetrahydropyranyloxy)-hexanoate (prepared as described in Reference Example 6) in 70 ml. of absolute tetrahydrofuran were added dropwise to the solution at −70° C. and the reaction mixture was stirred at the same temperature for 2 hours and then for 16 hours at 4° C.

The reaction mixture was acidified with acetic acid and concentrated under reduced pressure. The residue was dissolved in a small amount of water and extracted with diethyl ether. The ethereal extracts were dried over magnesium sulphate and concentrated under reduced pressure. The residue was distilled at 45° to 59° C. at a pressure of 2 to 4 mm.Hg. The resulting residue was purified by column chromatography on silica gel using ethyl acetate as eluent to give 14.0 g. of the title compound having the following physical characteristics:

IR (liquid film); ν: 2930, 2850, 1715, 1455, 1445, 1375, 1365, 1330, 1260, 1200, 1180, 1140, 1120, 1035, 990 cm$^{-1}$;

NMR (CDCl$_3$ solution); δ: 4.70–4.40 (1H, m), 4.15–3.10 (4H, m), 3.77 (6H, d), 3.10 (2H, d).

REFERENCE EXAMPLE 8

Methyl 9α-acetoxy-11α,20-bis-(2-tetrahydropyranyloxy)-15-oxo-16( ⟨ )-methylprosta-cis-5,trans-13-dienoate 1.79 g. of sodium hydride (55% content) were suspended in 240 ml. of absolute tetrahydrofuran. With stirring under an atmosphere of nitrogen at room temperature, 14.0 g. of dimethyl 2-oxo-3( ⟨ )-methyl-7-(2-tetrahydropyranyloxy)-heptylphosphonate (prepared as described in Reference Example 7) in 130 ml. of tetrahydrofuran were added to the solution, and the mixture stirred for 20 minutes.

14.4 g. of 1α-acetoxy-2α-(6-methoxycarbonylhex-cis-2-enyl)-3β-formyl-4α-(2-tetrahydropyranyloxy)-cyclopentane (prepared as described in Reference Example 3) in 65 ml. of tetrahydrofuran were added and stirred for one hour at room temperature. The reaction mixture was neutralised with acetic acid and filtered and the filtrate was concentrated under reduced pressure. The residue was purified by column chromatography on silica gel using a mixture of benzene and ethyl acetate (4:1) as eluent to give 19.8 g. of the title compound having the following physical characteristics:

IR (liquid film); ν: 2960, 2870, 1740, 1700, 1675, 1630, 1455, 1440, 1380, 1360, 1330, 1250, 1200, 1190–1150, 1140, 1125, 1080, 1045, 980 cm$^{-1}$;

NMR (CDCl$_3$ solution); δ: 6.64 (1H, q), 6.15 (1H, d), 5.60–5.12 (2H, m), 5.10–4.83 (1H, m), 4.83–4.35 (2H, m), 4.35–3.10 (6H, m), 3.62 (3H, s), 2.02 (3H, s);

TLC (developing solvent benzene:ethyl acetate = 2:1): Rf = 0.56.

REFERENCE EXAMPLE 9

Methyl 9α-acetoxy-11α,20-bis-(2-tetrahydropyranyloxy)-15α-hydroxy-16( ⟨ )-methylprosta-cis-5,trans-13-dienoate and the 5β-hydroxy epimer 19.8 g. of methyl 9α-acetoxy-11α,20-bis-(2-tetrahydropyranyloxy)-15-oxo-16( ⟨ )-methylprosta-cis-5,trans-13-dienoate (prepared as described in Reference Example 8) in 320 ml. of methanol were cooled to −30° C. to −40° C. with stirring. 4.28 g. of sodium borohydride were added in portions. The reaction mixture was then stirred at the same temperature for 30 minutes, and then neutralised with acetic acid. The solvent was removed and the residue was extracted with ethyl acetate. The extracts were washed with an aqueous sodium bicarbonate solution, dried over magnesium sulphate and concentrated under reduced pressure. The residue was purified by column chromatography on silica gel using a mixture of benzene and ethyl acetate as eluent to give 7.80 g. of the title compound, 7.13 g. of the 15β-hydroxy epimer and 4.1 g. of a mixture of them. TLC of the title compound and 15β-hydroxy epimer gave the following results:

TLC (developing solvent benzene:ethyl acetate = 1:1):
the 15α-hydroxy compound: Rf = 0.54,
the 15β-hydroxy compound: Rf = 0.64.

The title compound had the following physical characteristics:

IR (liquid film); ν: 3450, 2950, 2860, 1740, 1455, 1380, 1355, 1330, 1250, 1200, 1145, 1125, 1080, 1035, 980 cm$^{-1}$;

NMR (CDCl$_3$ solution); δ: 5.65–5.12 (4H, m), 5.12–4.80 (1H, m), 4.75–4.30 (2H, m), 4.30–3.10 (8H, m), 3.60 (3H, s), 2.02 (3H, s).

REFERENCE EXAMPLE 10

Methyl 9α-acetoxy-11α,15α,20-tri-(2-tetrahydropyranyloxy)-16( ⟨ )-methylprosta-cis-5,trans-13-dienoate 7.90 g. of methyl 9α-acetoxy-11α,20-bis-(2-tetrahydropyranyloxy)-15α-hydroxy-16( ⟨ )-methylprosta-cis-5,trans-13-dienoate (prepared as described in Reference Example 9) were dissolved in 80 ml. of methylene chloride and the solution was reacted with 2.0 ml. of dihydropyran and 37 mg. of p-toluenesulphonic acid at 25° C., for 30 minutes to give 7.2 g. of the title compound having the following physical characteristics:

IR (liquid film); ν: 2950, 2860, 1745, 1460, 1445, 1380, 1340, 1250, 1200, 1190, 1165, 1140, 1080, 1045, 1030, 980 cm$^{-1}$;

NMR (CDCl$_3$ solution); δ: 5.65–5.10 (4H, m), 5.10–4.80 (1H, m), 4.80–4.32 (3H, m), 4.24–3.10 (10H, m), 3.60 (3H, s), 2.00 (3H, s);

TLC (developing solvent benzene:ethyl acetate = 1:1): Rf = 0.79.

EXAMPLE 12

9α-Hydroxy-11α,15α,20-tri-(2-tetrahydropyranyloxy)-16( ⟨ )-methylprosta-cis-5,trans-13-dienoic acid 7.2 g. of methyl 9α-acetoxy-11α,15α,20-tri-(2-tetrahydropyranyloxy)-16( ⟨ )-methylprosta-cis-5,trans-13-dienoate (prepared as described in Reference Example 10) were dissolved in a solution of 4.2 g. of potassium hydroxide in a mixture of 7.0 ml. of water and 28 ml. of methanol and stirred at room temperature for 2 hours. The reaction mixture was neutralised with oxalic acid, extracted with ethyl acetate, washed with water, dried over magnesium sulphate and concentrated under reduced pressure. The residue was purified by column chromatography on silica gel using a mixture of benzene and ethyl acetate (1:2) as eluent to give b 5.2 g. of the title compound having the following physical characteristics:

IR (liquid film); ν: 3450, 2950, 1860,–2300, 1740, 1715, 1455, 1380, 1360, 1330, 1250, 1200, 1185, 1140, 1125, 1080, 1040, 980 cm$^{-1}$;

NMR (CDCl$_3$ solution); δ: 6.35 (2H, broad s), 5.70–5.14 (4H, m); 4.85–4.30 (4H, m), 4.30–3.00 (11H, m);

TLC (developing solvent benzene:ethyl acetate = 1:2): Rf = 0.14.

EXAMPLE 13

16( ⟨ )-Methyl-20-hydroxy-PGF$_{2α}$ 860 mg. of 9α-hydroxy-11α,15α,20-tri-(2-tetrahydropyranyloxy)-16( ⟨ )-methylprosta-cis-5,trans-13-dienoic acid (prepared as described in Example 12) were dissolved in 33 ml. of a mixture of acetic acid, water and tetrahydrofuran 65:35:10), and the resulting solution was stirred vigorously at 45° C. for 2 hours. The reaction mixture was concentrated under reduced pressure. The residue was mixed with toluene and the acetic acid was removed by azeotropic distillation. After the treatment had finished, the residue was purified by column chromatography on silica gel using ethyl acetate as eluent to give 325 mg. of the title compound having the following physical characteristics:

IR (liquid film); ν: 3360, 2925, 2855, 1710, 1415, 1382, 1250, 1080, 1040, 978 cm$^{-1}$;

NMR (CDCl$_3$ + deutero dimethylsulphoxide solution); δ: 5.65–5.20 (4H, m), 4.65–3.75 (8H, m), 3.59 (2H, t), 1.0–0.75 (3H, m);

TLC (developing solvent ethyl acetate:formic acid = 400:5): Rf = 0.10.

EXAMPLE 14

9-Oxo-11α,15α,20-tri-(2-tetrahydropyranyloxy)-16(ξ)-methylprosta-cis-5,trans-13-dienoic acid 2.14 g. of 9α-hydroxy-11α,15α,20-tri-(2-tetrahydropyranyloxy)-16(ξ)-methylprosta-cis-5,trans-13-dienoic acid (prepared as described in Example 12) were dissolved in 70 ml. of diethyl ether. The solution was cooled to 0° to 5° C. and then a chromic acid solution (prepared by dissolving 12.4 g. of chromium trioxide, 41 g. of manganese sulphate and 3.0 ml. of sulphuric acid in 51 ml. of water) was added and the reaction mixture was stirred vigorously at 0° to 5° C. for 40 minutes.

The reaction mixture was diluted with diethyl ether and the aqueous layer was separated. The aqueous layer was extracted with diethyl ether. The combined extracts were washed sufficiently with water until the washing was not coloured yellow, dried over sodium sulphate and then concentrated under reduced pressure. The residue was purified by column chromatography on silica gel using a mixture of benzene and ethyl acetate (2:1) as eluent to give 1.73 g. of the title compound having the following physical characteristics:

IR (liquid film); ν: 2940, 2870,–2300, 1745, 1715, 1455, 1445, 1390, 1360, 1325, 1270, 1210, 1195, 1080, 1040, 1025, 980 cm$^{-1}$;

NMR (CDCl$_3$ solution); δ: 8.68 (1H, s), 5.75–5.10 (4H, m), 4.90–4.40 (3H, m), 4.35–3.15 (10H, m);

TLC (developing solvent benzene:ethyl acetate = 2:3): Rf = 0.53.

EXAMPLE 15

16(ξ)-Methyl-20-hydroxy-PGE$_2$ 1.73 g. of 9-oxo-11α,15α,20-tri-(tetrahydropyranyloxy)-16(ξ)-methyl-prosta-cis-5,trans-13-dienoic acid (prepared as described in Example 14) were dissolved in 55 ml. of a mixture of acetic acid, water and tetrahydrofuran (65:35:10) and stirred at 40° C. for one hour. The reaction mixture was then mixed with toluene, and acetic acid was removed by azeotropic distillation. The residue was purified by column chromatography on silica gel using a mixture of ethyl acetate and ethanol (40:1) as eluent to give 690 mg. of the title compound having the following physical characteristics:

IR (liquid film); ν: 3360, 2925, 2855, 1710, 1415, 1382, 1250, 1080, 1040, 978 cm$^{-1}$;

NMR (CDCl$_3$ solution); δ: 5.70–5.20 (4H, m), 4.57 (4H, broad s), 4.15–3.80 (2H, m), 3.61 (2H, t), 1.0–0.75 (3H, m);

TLC (developing solvent chloroform:tetrahydrofuran:acetic acid = 10:2:1): Rf = 0.05.

EXAMPLE 16

9α-Hydroxy-11α,15α,20-tri-(2-tetrahydropyranyloxy)-16(ξ)-methylprost-trans-13-enoic acid 0.5 g. of 5% palladium on charcoal was suspended in 50 ml. of methanol. Air in the apparatus was replaced with hydrogen and 2.20 g. of 9α-hydroxy-11α,15α,20-tri-(2-tetrahydropyranyloxy)-16(ξ)-methylprosta-cis-5,trans-13-dienoic acid (prepared as described in Example 12) were added.

Catalytic reduction of the compound was carried out at room temperature under ambient pressure. After completion of the reaction, the catalyst was separated by filtration and the filtrate was evaporated under reduced pressure to give 1.85 g. of the title compound having the following physical characteristics:

NMR (CDCl$_3$ solution); δ: 6.73 (2H, s), 5.70–5.27 (2H, m), 4.85–4.35 (3H, m), 4.35–3.05 (11H, m);

TLC: The product and the starting material behaved similarly on silica gel plate. After hydrolysis by the same method as described in Example 6, the result of thin layer chromatography with a plate impregnated with silver nitrate by using a mixture of ethyl acetate, methanol and acetic acid (10:1:1) as developing solvent was Rf 0.29. On the other hand, using the said starting material, the resulting Rf was 0.15.

EXAMPLE 17

9-Oxo-11α,15α,20-tri-(2-tetrahydropyranyloxy)-16(ξ)-methylprost-trans-13-enoic acid 1.85 g. of 9α-hydroxy-11α,15α,20-tri-(2-tetrahydropyranyloxy)-16(ξ)-methylprost-trans-13-enoic acid (prepared as described in Example 16) were dissolved in 50 ml. of diethyl ether. The solution was cooled to 0° to 5° C. and then 45 ml. of a chromic acid solution (prepared by dissolving 3.2 g. of chromium trioxide, 10.8 g. of manganese sulphate and 3.56 ml. of sulphuric acid in water to make the total volume 80 ml.) were added and the reaction mixture was stirred vigorously at 0° to 5° C. for one hour. The reaction mixture was diluted with diethyl ether and the aqueous layer was separated. The aqueous layer was extracted with diethyl ether. The combined ethereal extracts were washed with water sufficiently until the washing was not coloured yellow, dried over magnesium sulphate and concentrated under reduced pressure. The residue was purified by column chromatography on silica gel using a mixture of benzene and ethyl acetate (2:1) as eluent to give 1.43 g. of the title compound having the following physical characteristics:

IR (liquid film); ν: 2930, 2850,–2350, 1745, 1715, 1455, 1440, 1380, 1360, 1330, 1265, 1200, 1190, 1160, 1140, 1085, 980 cm$^{-1}$;

NMR (CDCl$_3$ solution); δ: 9.30 (1H, s), 5.85–5.35 (2H, m), 4.85–4.45 (3H, m), 4.40–3.05 (10H, m);

TLC (developing solvent benzene:ethyl acetate = 2:3): Rf = 0.58.

EXAMPLE 18

16(ξ)-Methyl-20-hydroxy-PGE$_1$ 1.43 g. of 9-oxo-11α,15α,20-tri-(2-tetrahydropyranyloxy)-16(ξ)-methylprost-trans-13-enoic acid (prepared as described in Example 17) were dissolved in 44 ml. of a mixture of acetic acid, water and tetrahydrofuran (65:35:10) and stirred at 38° to 40° C. for 2 hours. The reaction mixture, to which toluene was added to remove the acetic acid by azeotropic distillation, was then concentrated in vacuo. The residue was purified by column chromatography on silica gel using a mixture of ethyl acetate and ethanol (40:1) as eluent to give 510 mg. of the title compound having the following physical characteristics:

IR (liquid film); ν: 3360, 2925, 2850, 1745, 1710, 1460, 1410, 1250, 1165, 1080, 980 cm$^{-1}$;

NMR (CDCl$_3$ solution); δ: 5.70–5.45 (2H, m), 4.90 (4H, broad s), 4.15–3.75 (2H, m), 3.59 (2H, t), 0.98–0.75 (3H, m);

TLC (developing solvent chloroform:tetrahydrofuran:acetic acid = 10:2:1): Rf = 0.07.

EXAMPLE 19

16($\xi$)-Methyl-20-hydroxy-PGE$_1$ methyl ester 265 mg. of 16($\xi$)-methyl-20-hydroxy-PGE$_1$ (prepared as described in Example 18) were dissolved in a mixture of 5 ml. of methylene chloride and 5 ml. of ethyl acetate and freshly prepared diazomethane solution in diethyl ether was added until the yellow colour did not disappear. The reaction mixture was concentrated under reduced pressure and the residue was purified by column chromatography on silica gel using ethyl acetate as eluent to give 195 mg. of the title compound having the following physical characteristics:

IR (liquid film); ν: 3350, 2920, 2850, 1740, 1460, 1440, 1380, 1250, 1200, 1170, 1080, 1035, 975 cm$^{-1}$;

NMR (CDCl$_3$ solution); δ: 5.82–5.45 (2H, m), 4.24–3.79 (2H, m), 3.67 (3H, t), 3.79–3.40 (2H, m), 1.00–0.70 (3H, t).

TLC (developing solvent chloroform:tetrahydrofuran:acetic acid = 10:2:1): Rf = 0.13.

The methyl esters of other prostaglandin analogues conforming to general formula VII, for example those products of Examples 2, 4, 5, 8, 11, 13 and 15, can be prepared in a similar way.

EXAMPLE 20

16($\xi$)-Methyl-20-hydroxy-PGE$_1$ triethanolamine salt 14.6 mg. of 16($\xi$)-methyl-20-hydroxy-PGE$_1$ (prepared as described in Example 18) were dissolved in 2 ml. of ethyl acetate and 5.8 mg. of triethanolamine was added to the reaction mixture, which was concentrated under reduced pressure to give 19.8 mg. of the title compound.

EXAMPLE 21

16($\xi$)-Methyl-20-hydroxy-13,14-dihydro-PGE$_1$ methyl ester 90 mg. of 16($\xi$)-Methyl-20-hydroxy-PGE$_1$ methyl ester (prepared as described in Example 19) were dissolved in 3 ml. of methanol. Then 20 mg. of 5% palladium on charcoal were added to the solution. The reaction mixture was stirred with hydrogen at room temperature under ambient pressure for 2 hours. The catalyst was separated by filtration and the filtrate was concentrated under reduced pressure. The residue was purified by column chromatography on silica gel using a mixture of ethyl acetate and benzene (3:1) as eluent to give 60 mg. of the title compound having the following physical characteristics:

IR (liquid film); ν: 3400, 2920, 2850, 1740, 1450, 1250, 1180, 1050 cm$^{-1}$;

NMR (CDCl$_3$ solution); δ: 4.30–3.90 (1H, m), 3.90–3.30 (6H, m), 2.85–2.50 (1H, d-d), 2.50–2.10 (4H, m), 1.00–0.80 (3H, d);

TLC (developing solvent ethyl acetate:formic acid = 400:5): Rf = 0.25.

The present invention includes within its scope pharmaceutical compositions which comprise at least one pharmacologically active cyclopentane derivative of general formula VII, or a cyclodextrin clathrate, or, when R represents a hydrogen atom, a non-toxic salt thereof, together with a pharmaceutical carrier or coating. In clinical practice such novel compounds will normally be administered orally, rectally, vaginally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the adult, the daily dose for the treatment of hypertension and disorders of the peripheral circulation by oral administration are generally between 0.1 μg. and 100 μg/kg. body weight, between 0.1 μg. and 100 μg./kg. body weight by oral administration in the prevention and treatment of cerebral thrombosis and myocardial infarction, between 0.5 and 100 μg./kg. body weight by oral administration in the treatment of gastric ulceration, and between 10 μg. and 5 mg./kg. body weight by oral, intravaginal, intravenous and extraamniotic administration for contraception, menstrual regulation, abortion and the induction of labour in pregnant female mammals, and for the treatment of asthma between 10 μg. and 200 μg., between 50 μg. and 500 μg., and between 0.1 μg. and 2 μg., by administration by means of an aerosol, or orally or intravenously, respectively, per person.

Prostaglandin compounds according to the present invention may be administered orally by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. Advantageously, the solution to be nebulized is diluted, and aqueous solutions containing from 1 to 100 μg., and more particularly 10 to 50 μg., of active ingredient per ml. of solution are particularly suitable. The solution may contain stabilizing agents such as sodium bisulphite and buffering agents to give it an isotonic character, e.g. sodium chloride, sodium citrate and citric acid.

The active ingredients may also be administered orally by inhalation in the form of aerosols generated from self-propelling pharmaceutical compositions. Compositions suitable for this purpose may be obtained by dissolving or suspending in finely-divided form, preferably micronized to an average particle size of less than 5 microns, the active ingredients in pharmaceutically-acceptable solvents, e.g. ethanol, which are co-solvents assisting in dissolving the active ingredients in the volatile liquid propellants hereinafter described, or pharmaceutically-acceptable suspending or dispersing agents, for example aliphatic alcohols such as oleyl alcohol, and incorporating the solutions or suspensions obtained with pharmaceutically-acceptable volatile liquid propellants, in conventional pressurized packs which may be made of any suitable material, e.g. metal, plastics or glass, adequate to withstand the pressures generated by the volatile propellant in the pack. Pressurized pharmaceutically-acceptable gases, such as nitrogen, may also be used as propellants. The pressurized pack is preferably fitted with a metered valve which dispenses a controlled quantity of the self-propelling aerosol composition as a single dose.

Suitable volatile liquid propellants are known in the art and include fluorochlorinated alkanes containing from one to four, and preferably one or two, carbon atoms, for example dichlorodifluoromethane, dichlorotetrafluoroethane, trichloromonofluoromethane, dichloromonofluoromethane and monochlorotrifluoromethane. Preferably, the vapour pressure of the volatile liquid propellant is between about 25 and 65 pounds, and more especially between about 30 and 55 pounds, per square inch gauge at 21° C. As is well-known in the art, volatile liquid propellants of different vapour pressures may be mixed in varying proportions to give a propellant having a vapour pressure appropriate to the production of a satisfactory aerosol and suitable for the chosen container. For example, dichlorodifluoromethane (vapour pressure 85 pounds per square inch gauge at 21° C.) and dichlorotetrafluoroethane (vapour pressure 28 pounds per square inch gauge at 21° C.) may be mixed in varying proportions to give propellants having vapour pressures intermediate between those of two constituents, e.g. a mixture of dichlorodifluoromethane and dichlorotetrafluoroethane in the proportions 38:62 respectively by weight has a vapour pressure of 53 pounds per square inch gauge at 21° C.

The self-propelling pharmaceutical compositions may be prepared by dissolving the required quantity of active ingredient in the co-solvent or combining the required quantity of active ingredient with a measured quantity of suspending or dispersing agent. A measured quantity of this composition is then placed in an open container which is to be used as the pressurized pack. The container and its contents are then cooled below the boiling temperature of the volatile propellant, to be used. The required quantity of liquid propellant, cooled below its boiling temperature, is then added and the contents of the container mixed. The container is then sealed with the required valve fitting, without allowing the temperature to rise above the boiling temperature of the propellant. The temperature of the sealed container is then allowed to rise to ambient with shaking to ensure complete homogeneity of the contents to give a pressurized pack suitable for generating aerosols for inhalation. Alternatively, the co-solvent solution of the active ingredient or combination of active ingredient and suspending or dispersing agent is placed in the open container, the container sealed with a valve, and the liquid propellant introduced with pressure.

Means for producing self-propelling compositions for generating aerosols for the administration of medicaments are, for example, described in detail in U.S. Pat. Nos. 2,868,691 and 3,095,355.

Preferably, the self-propelling pharmaceutical compositions according to the present invention contain from 1 to 100 μg., and more particularly 10 to 50 μg., of active ingredient per ml. of solution or suspension It is important that the pH of solutions and suspensions used, according to the present invention, to generate aerosols should be kept within the range 3 to 8 and preferable that they should be stored at or below 4° C., to avoid pharmacological deactivation of the active ingredient.

EXAMPLE 22

16($\zeta$)-Methyl-20-hydroxy-PGE$_1$ (500 μg.) was dissolved in ethanol (1 ml.) and the solution obtained was added to an aqueous solution (12 ml.) containing sodium carbonate (50 mg.). Aqueous sodium chloride solution (0.9 w/v, 2 ml.) was then added to give a final volume of 15 ml. The solution was then sterilized by passage through a bacteria-retaining filter and placed in 1.5 ml. portions in 5 ml. ampoules, to give 50 μg. of 16($\zeta$)-methyl-20-hydroxy-PGE$_1$ (in the form of its sodium salt) per ampoule. The contents of the ampoules were freeze-dried and the ampoules sealed. The contents of an ampoule in a suitable volume, e.g. 2 ml., of sterile water or physiological saline gave a solution ready for administration by injection.

EXAMPLE 23

16($\zeta$)-Methyl-20-hydroxy-PGE$_1$ (20 mg.) was dissolved in ethanol (10 ml.), mixed with mannitol (18.5 g.), sieved through a 30-mesh sieve, dried at 30° C. for 90 minutes and again sieved through a 30-mesh sieve. Aerosil (microfine silica; 200 mg.) was added and the powder obtained was machine-filled into one hundred No. 2 hard gelatin capsules to give capsules each containing 200 μg. of 16($\zeta$)-methyl-20-hydroxy-PGE$_1$, which after swallowing of the capsules is released into the stomach.

EXAMPLE 24

A solution of 16($\langle$)-methyl-20-hydroxy-PGE$_1$ (4.5 mg.) in absolute ethanol (0.45 ml.) was placed in a polyvinylchloride-coated glass bottle (20 ml. volume), the bottle cooled to a low temperature (−60° C.) and dichlorodifluoromethane (3.7 ml.; 4.9 g.) and dichlorotetrafluoroethane (4.85 ml.; 7.3 g.), cooled to the liquid state, added to give a self-propelling composition (9 ml.) containing 0.5 mg. of 16($\langle$)-methyl-20-hydroxy-PGE$_1$/ml. of solution.

The bottle was sealed with a metered valve (with dip tube) delivering 55 μl. doses and the contents rendered homogeneous by shaking, while allowing the temperature of the bottle and its contents to return to ambient. Each 'puff' (generated from 55 μl. of solution) of aerosol released from the pressurized pack thus obtained contained 27.5 μg. of 16($\langle$)-methyl-20-hydroxy-PGE$_1$.

EXAMPLE 25

Proceeding as in Example 24 but replacing the solution of 16($\langle$)-methyl-20-hydroxy-PGE$_1$ (4.5 mg.) in absolute ethanol (0.45 ml.) by a solution ten times more dilute, i.e. 16($\langle$)-methyl-20-hydroxy-PGE$_1$ (0.45 mg.) in absolute ethanol (0.45 ml.), a pressurized pack containing 0.05 mg. of 16($\langle$)-methyl-20-hydroxy-PGE$_1$/ml. of solution was obtained, from which each 'puff' (generated from 55 μl. of solution) of aerosol released contained 2.75 μg. of 16($\langle$)-methyl-20-hydroxy-PGE$_1$.

What is claimed is:

1. A compound of the formula:

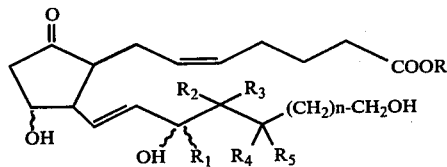

wherein R represents a hydrogen atom or a straight- or branched-chain alkyl group containing from 1 to 12 carbon atoms, $R^1$, $R^2$, $R^3$, $R^4$ and $R^5$, which may be the same or different, each represents a hydrogen atom or a methyl or ethyl group, and n represents zero or an integer from 1 to 3 inclusive, and cyclodextrin clathrates of such acids and esters and, when R represents a hydrogen atom, the non-toxic salts thereof.

2. A compound of the formula:

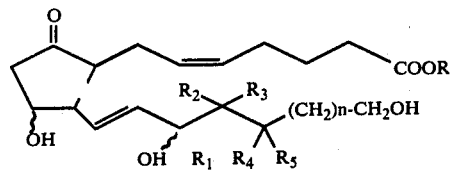

wherein R represents a hydrogen atom or a straight- or branched-chain alkyl group containing from 1 to 12 carbon atoms, $R^1$, $R^2$, $R^3$, $R^4$ and $R^5$, which may be the same or different, each represent a hydrogen atom or a methyl or ethyl group, and n represents zero or an integer from 1 to 3 inclusive, and cyclodextrin clathrates of such acids and esters and, when R represents a hydrogen atom, the non-toxic salts thereof.

3. A compound of the formula:

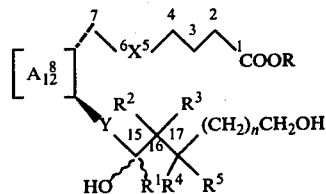

wherein A represents a grouping of the formula:

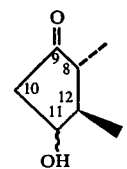

and X represents ethylene and Y represents trans-vinylene, R represents a hydrogen atom or a straight- or branched-chain alkyl group containing from 1 to 12 carbon atoms, $R^1$, $R^2$, $R^3$, $R^4$ and $R^5$, which may be the same or different, each represent a hydrogen atom or a methyl or ethyl group, and n represents zero or an integer from 1 to 3 inclusive, and cyclodextrin clathrates of such acids and esters and, when R represents a hydrogen atom, the non-toxic salts thereof.

4. A compound according to claim 1 wherein R represents a hydrogen atom or a methyl group.

5. A compound according to claim 1 wherein n is 2.

6. A compound according to claim 1 wherein one of the symbols $R^1$, $R^2$, $R^3$, $R^4$ and $R^5$ represents a hydrogen atom or a methyl group, and the other symbols represent hydrogen atoms.

7. A compound according to claim 1 wherein $R^1$ represents a hydrogen atom, $R^2$ represents a hydrogen atom or a methyl group, and $R^3$, $R^4$ and $R^5$ represent hydrogen atoms.

8. A compound according to claim 1 wherein the hydroxy group attached to the C-15 carbon atom of formula VII depicted in claim 1 is in α-configuration.

9. A compound according to claim 1 wherein the hydroxy group attached to the 11-position of the cyclopentane ring of formula VIIIA depicted in claim 1 is in the α-configuration.

10. A compound according to claim 1 which is 20-hydroxy-PGE$_1$.

11. A compound according to claim 1 which is 16( )-methyl-20-hydroxy-PGE$_1$.

* * * * *